(12) United States Patent
Klun et al.

(10) Patent No.: US 10,000,626 B2
(45) Date of Patent: Jun. 19, 2018

(54) STERICALLY HINDERED AMINE AND OXYALKYL AMINE LIGHT STABILIZERS

(71) Applicant: 3M INNOVATIVE PROPERTIES COMPANY, St. Paul, MN (US)

(72) Inventors: Thomas P. Klun, Lakeland, MN (US); Mark A. Roehrig, Stillwater, MN (US); Joseph C. Spagnola, Woodbury, MN (US); Alan K. Nachtigal, Maplewood, MN (US); Charles J. Hoy, Maple Plain, MN (US); Richard J. Pokorny, Maplewood, MN (US); William J. Hunt, Afton, MN (US); Jason T. Petrin, Woodbury, MN (US); Paul B. Armstrong, St. Paul, MN (US); Suresh S. Iyer, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days. days.

(21) Appl. No.: 15/532,663

(22) PCT Filed: Dec. 14, 2015

(86) PCT No.: PCT/US2015/065470
§ 371 (c)(1),
(2) Date: Jun. 2, 2017

(87) PCT Pub. No.: WO2016/105990
PCT Pub. Date: Jun. 30, 2016

(65) Prior Publication Data
US 2017/0355833 A1    Dec. 14, 2017

Related U.S. Application Data

(60) Provisional application No. 62/095,458, filed on Dec. 22, 2014.

(51) Int. Cl.
*C08K 5/544* (2006.01)
*C07F 7/18* (2006.01)
*C08K 9/06* (2006.01)
*C08K 3/36* (2006.01)
*C07D 211/46* (2006.01)
*C08K 5/3435* (2006.01)
*C07D 211/94* (2006.01)
*C07D 211/58* (2006.01)

(52) U.S. Cl.
CPC .......... *C08K 5/5442* (2013.01); *C07D 211/46* (2013.01); *C07D 211/58* (2013.01); *C07D 211/94* (2013.01); *C07F 7/1836* (2013.01); *C08K 3/36* (2013.01); *C08K 5/3435* (2013.01); *C08K 9/06* (2013.01)

(58) Field of Classification Search
CPC .. C08K 5/5442; C08K 5/3435; C07D 211/46; C07D 211/58; C07D 211/94
See application file for complete search history.

(56) References Cited

U.S. PATENT DOCUMENTS

| | | | |
|---|---|---|---|
| 3,904,581 A * | 9/1975 | Murayama | C07D 211/58 524/103 |
| 4,356,296 A | 10/1982 | Griffith | |
| 4,642,126 A | 2/1987 | Zador | |
| 4,648,843 A | 3/1987 | Mitra | |
| 4,652,274 A | 3/1987 | Boettcher | |
| 4,665,217 A | 5/1987 | Reiners | |
| 4,752,338 A | 6/1988 | Reiners | |
| 4,983,737 A | 1/1991 | Ravichandran | |
| 5,026,902 A | 6/1991 | Fock | |
| 5,076,844 A | 12/1991 | Fock | |
| 5,219,905 A * | 6/1993 | Carrozza | C07F 7/0854 524/102 |
| 5,286,865 A | 2/1994 | Galbo | |
| 5,354,808 A | 10/1994 | Onwumere | |
| 5,359,069 A | 10/1994 | Galbo | |
| 5,442,071 A | 8/1995 | Galbo | |
| 6,566,413 B1 | 5/2003 | Weinmann | |
| 6,572,969 B1 | 6/2003 | Samaranayake | |
| 6,624,236 B1 | 9/2003 | Bissinger | |
| 6,852,795 B2 | 2/2005 | Bissinger | |
| 6,852,822 B1 | 2/2005 | Bissinger | |
| 7,101,616 B2 | 9/2006 | Arney | |
| 7,718,264 B2 | 5/2010 | Klun | |
| 2002/0058735 A1 | 5/2002 | Galbo | |
| 2002/0115754 A1 | 8/2002 | Desai | |
| 2003/0187091 A1 | 10/2003 | Moszner | |
| 2010/0249401 A1 | 9/2010 | Schöning | |

(Continued)

FOREIGN PATENT DOCUMENTS

| | | |
|---|---|---|
| EP | 0665233 | 8/1995 |
| EP | 2716666 | 4/2014 |

(Continued)

OTHER PUBLICATIONS

Habicher (New stabilisers for polymers on the basis of isophorone diisocyanate. Polymer Degradation and Stability, 68, 2000, pp. 127-132).*
Amamoto, "Programmed Thermodynamic Formation and Structure Analysis of Star-like Nanogels with Core Cross-linked by Thermally Exchangeable Dynamic Covalent Bonds", Journal of The American Chemical Society, 2007, vol. 129, No. 43, pp. 13298-13304, (XP002754413).
Borch, "The Cyanohydridoborate Anion as a Selective Reducing Agent", Journal of The American Chemical Society, Jun. 16, 1971, vol. 93, No. 12, pp. 2897-2904.
Borch, "Reductive Amination With Sodium Cyanoborohydride: N,N- Dimethylcyclohexylamine", Organic Syntheses, Coll., 1988, vol. 6: p. 499; 1972, vol. 52, p. 124 (5 pages).

(Continued)

*Primary Examiner* — Brieann R Johnston
(74) *Attorney, Agent, or Firm* — Jean A. Lown

(57) ABSTRACT

The present disclosure relates to sterically hindered alkyl amine and sterically hindered oxyalkyl amine compounds, as well as particles, substrates, coatings, and articles including the same.

14 Claims, No Drawings

(56) References Cited

U.S. PATENT DOCUMENTS

| | | | |
|---|---|---|---|
| 2014/0295724 A1 | 10/2014 | Sworen | |
| 2015/0203707 A1* | 7/2015 | Klun | C07F 7/1868 428/412 |
| 2015/0344504 A1* | 12/2015 | Klun | C07F 7/1868 428/1.51 |

FOREIGN PATENT DOCUMENTS

| | | |
|---|---|---|
| GB | 2351732 | 1/2001 |
| JP | 2001-270859 | 10/2001 |
| JP | 2010-215902 | 9/2010 |
| WO | 2015/051217 | 4/2015 |
| WO | 2016/105974 | 6/2016 |
| WO | 2016/105988 | 6/2016 |
| WO | 2016/105993 | 6/2016 |

OTHER PUBLICATIONS

Jang, "Synthesis and Performance of Reactive Light Stabilizers for Weather-Resistant UV-Curable Coatings", Journal of Industrial and Engineering Chemistry, 2005, vol. 11, No. 6, pp. 964-970, (XP009188746).

Kuroboshi, "Electrooxidation of Alcohols in N-Oxyl-Immobilized Silica Gel/Water Disperse System: Approach to Totally Closed System", Synthesis, Mar. 2009, vol. 2009, No. 6, pp. 903-908, (XP002754414).

Ling, "Synthesis and Characterization of new Monomers and Polymers Containing Hindered Piperidine Groups", Journal of Macromolecular Science, Part A: Pure and Applied Chemistry, 1998, vol. 35, Nos. 7 & 8, pp. 1327-1336.

Ling, "Synthesis and Polymerization of New Methacryloyl Ureas Carrying a Hindered Piperidine and a Hydroxyl Group", Journal of Macromolecular Science, Part A: Pure and Applied Chemistry, 2001, vol. 38, No. 2, pp. 137-158.

Negishi, "Superior Light Stabilization Using a Novel Hindered Amine Light Stabilizer", Addcon World 2007, International Plastics Additives and Compounding Conference, 13th, Frankfurt, Germany, Sep. 5-6, 2007, Smithers Rapra Technology, Ltd., Shrewsbury, UK, pp. 9/1-9/8, (XP008176823).

Omura, "Oxidation of Alcohols by "Activated" Dimethyl Sulfoxide. A Preparative, Steric and Mechanistic Study", Tetrahedron, 1978, vol. 34, No. 11, pp. 1651-1660.

Schoening, "Synthetic Studies on N-Alkoxyamines: A Mild and Broadly Applicable Route Starting from Nitroxide Radicals and Aldehydes", Journal of Organic Chemistry, Feb. 2009, vol. 74, No. 4, pp. 1567-1573, (XP002754415).

Tidwell, "Oxidation of Alcohols by Activated Dimethyl Sulfoxide and Related Reactions: An Update", Synthesis, Oct. 1990, vol. 1990, No. 10, pp. 857-870.

International Search Report for International Application No. PCT/US2015/065470, dated Mar. 10, 2016, 5 pages.

* cited by examiner

STERICALLY HINDERED AMINE AND OXYALKYL AMINE LIGHT STABILIZERS

CROSS REFERENCE TO RELATED APPLICATIONS

This application is a national stage filing under 35 U.S.C. 371 of PCT/US2015/065470, filed Dec. 14, 2015, which claims the benefit of U.S. Provisional Application No. 62/095,458, filed Dec. 22, 2014, the disclosure of which is incorporated by reference in its/their entirety herein.

TECHNICAL FIELD

The present disclosure relates to sterically hindered alkyl amine and sterically hindered oxyalkyl amine compounds.

BACKGROUND

Compounds containing sterically hindered alkyl amines or sterically hindered oxyalkyl amines, and particularly the moiety

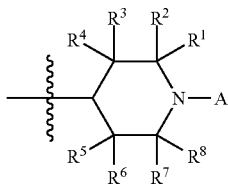

wherein $R^1$ is alkyl, $R^2$ is alkyl, $R^3$ is H or alkyl, $R^4$ is H or alkyl, $R^5$ is H or alkyl, $R^6$ is H or alkyl, $R^7$ is alkyl, and $R^8$ is alkyl are known. When A is alkyl, such compounds are known as hindered amine light stabilizers, or HALS; when A is oxyalkyl, such compounds are known as NORHALS.

The utility of HALS and NORHALS as radical scavengers and polymer stabilizers is well recognized in the art, and is described in, for example, the Journal of Macromolecular Science Part A, 35:7, 1327-36 (1998) and The Journal of Macromolecular Science Part A, 38:2, 137-58 (2001), as well as in JP 2001270859, U.S. Pat. No. 4,983,737 (Grant), and U.S. Pat. No. 5,442,071 (Grant). Such compounds are known to protect polymers from adverse effects of actinic radiation, such as visible and ultraviolet light.

SUMMARY

A compound can have the structure of Formula (I):

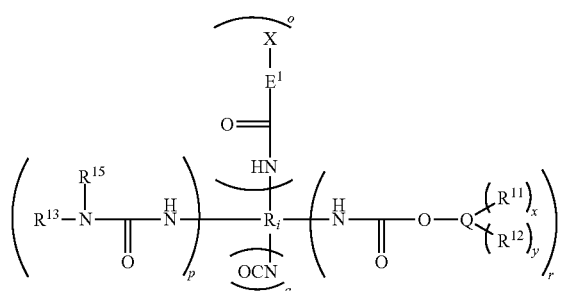

(I)

wherein $R_i$ is a residue of a multi-isocyanate;
$E^1$ is O or NR';
R' is H or $C_1$ to $C_4$ alkyl;
X is

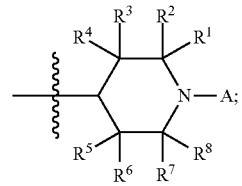

$R^1$ is alkyl;
$R^2$ is alkyl;
$R^3$ is H or alkyl;
$R^4$ is H or alkyl;
$R^5$ is H or alkyl;
$R^6$ is H or alkyl;
$R^7$ is alkyl;
$R^8$ is alkyl;
A is alkyl or oxyalkyl;
o is the number of $NHC(O)E^1X$ groups bound to $R_i$, which is between 1 and 9;
each Q is independently a connecting group having a valence of x+y+1;
each $R^{11}$ is independently an (alkyl)acrylolyoxy functional group of the formula $OC(O)C(R^d)=CH_2$, wherein each $R^d$ is independently alkyl or H;
x is the number of $R^{11}$ groups attached to a Q, which is from 0 to 6;
y is the number of $R^{12}$ groups attached to Q, which is from 0 to 6;
each $R^{12}$ is independently $-OC(O)CH(R^d)CH_2-R^a$ wherein $R^d$ is defined as above;
$R^a$ is $N(R^{16})_m(R^bSi(R^{14})_3)_n$;
$R^{16}$ is alkyl;
$R^b$ is alkylene that is also bound to the Si atom of $Si(R^{14})_3$;
each $R^{14}$ is independently selected from alkyl, oxyalkyl, $OC(O)R^d$, and hydroxyl, with the proviso that at least one $R^{14}$ is oxyalkyl, $OC(O)R^d$, or hydroxyl;
m is the number of $R^{16}$ groups bound to N, which is 0 to 1;
n is the number of $R^b$ groups bound to N, which is 1 or 2;
r is the number of

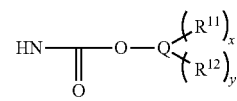

groups attached to $R_i$, which is from 0 to 6;
each $R^{13}$ is independently $R^cSi(R^{14})_3$;
each $R^c$ is independently alkylene, alkylene amine alkylene, or alkylene amine alkylene amine alkylene that is also bound to the Si atom of $Si(R^{14})_3$;
each $R^{15}$ is independently $R^{13}$, H, or alkyl;
p is the number of $R^{13}(R^{15})NC(O)NH$ groups bound to $R_i$, which is from 0 to 9;
q is the number of NCO groups covalently bound to $R_i$, which is from 0 to 8;
with the proviso that the sum of p+q+o+r is from 2 to 10;

with the proviso that the sum of p and y is at least 1; and with the proviso that when p is 0, x and y are both 0.

In addition to containing hindered alkyl or oxyalkyl amine groups, all of the compounds of Formula (I) feature one or more silyl groups. These groups allow the compounds of Formula (I) to be affixed to substrates, such as ceramic substrates, glass substrates, and silica substrates like silica nanoparticles.

DETAILED DESCRIPTION

Throughout this disclosure, singular forms such as "a," "an," and "the" are often used for convenience; however, it should be understood that the singular forms are meant to include the plural unless the singular alone is explicitly specified or is clearly indicated by the context.

Some terms used in this application have special meanings, as defined herein. All other terms will be known to the skilled artisan, and are to be afforded the meaning that a person of skill in the art at the time of the invention would have given them.

"Independently," when used in reference to the identity of one or more variable elements, means that each occurrence of any of the variable elements may have the same or different identity, within the specified limitations, regardless of the identity of any other occurrence of the reference element. Thus, if there are two occurrences of element "X," and element X can be independently selected from identity Y or identity Z, each of the two occurrences of X can be either Y or Z, in any combination (e.g., YY, YZ, ZY, or ZZ).

"Alkyl" refers to a saturated hydrocarbon radical. Many alkyl groups are from $C_1$ to $C_{30}$. Some alkyl groups can be $C_1$ or greater, such as $C_2$ or greater, $C_4$ or greater, $C_6$ or greater, or $C_8$ or greater. Some alkyl groups can be $C_{22}$ or smaller, $C_{16}$ or smaller, $C_{12}$ or smaller, $C_8$ or smaller, or $C_4$ or smaller. Unless otherwise indicated, any alkyl group can independently be linear, branched, cyclic, or a combination thereof (e.g., a cyclic alkyl can also have a linear or branched component). Exemplary alkyl groups include methyl, ethyl, propyl, isopropyl, n-butyl, t-butyl, sec-butyl, iso-butyl, 2-ethyl hexyl, iso-octyl, n-octyl, dodecyl, hexadecyl, behenyl, and the like.

"Oxyalkyl" refers to a monovalent radical having the formula O-alkyl, which can be referred to as an alkoxy group. The alkyl portion of the oxyalkyl can be any alkyl, such as those discussed above with reference to the definition of the term alkyl. Oxyalkyl can be written using standard prefixes to indicate the number of carbon atoms in the alkyl portion of the oxyalkyl. For example, oxymethyl is an oxyalkyl wherein the alkyl portion has one carbon, oxyethyl is an oxyalkyl wherein the alkyl portion has two carbons, etc. Oxyoctyl is an exemplary oxyalkyl that is often used in the compounds described herein.

"Alkylene" refers to an aliphatic hydrocarbon diradical (i.e., divalent radical). Many alkylene diradicals are from $C_1$ to $C_{30}$. Alkylene diradicals can be $C_1$ or greater, $C_2$ or greater, $C_3$ or greater, $C_4$ or greater, $C_6$ or greater, or $C_8$ or greater. Alkylene diradicals can be $C_{22}$ or smaller, $C_{16}$ or smaller, $C_{12}$ or smaller, $C_{10}$ or smaller, or $C_8$ or smaller. Unless otherwise indicated, any alkylene can be linear, branched or cyclic or a combination thereof (e.g., having both a cyclic component and a linear component). Exemplary alkylene groups include methylene, ethylene, propyl, isopropylene, n-butylene, t-butylene, sec-butylene, iso-butylene, 2-ethylhexylene, iso-octylene, dodecylene, hexadecylene, behenylene, and the like. In this application, hexylene is often used as an alkylene.

"Alkylene amine alkylene" refers to a moiety having the structure R—NH—R, wherein each R is independently alkylene. Each alkylene is typically $C_1$ to $C_{12}$, such as $C_1$ to $C_6$ or $C_1$ to $C_3$.

"Alkylene amine alkylene amine alkylene" refers to a moiety having the structure R—NH—R—NH—R, wherein each R is independently alkylene. Each alkylene is typically $C_1$ to $C_{12}$, such as $C_1$ to $C_6$ or $C_1$ to $C_3$.

"Isocyanate" refers to a molecule comprising at least one isocyanato radical, which is a —NCO radical.

A "multi-isocyanate" is an isocyanate molecule comprising at least two isocyanate radicals. As used herein, the multi-isocyanate is usually of formula $R_i(NCO)_{o+p+q+r}$ where the variables o, p, q, and r are defined for Formula (I). The residue $R_i$ is equal to the multi-isocyanate minus the isocyanato groups.

A polymer or copolymer is "derived from" a reference compound when the backbone of the polymer or copolymer contains a polymerized form of the reference compound.

A "hydrocarbon polyradical" as used herein is an aliphatic multivalent radical containing only carbon and hydrogen atoms. Hydrocarbon polyradicals can be $C_1$ or greater, $C_2$ or greater, $C_3$ or greater, $C_4$ or greater, $C_6$ or greater, or $C_8$ or greater. Hydrocarbon polyradicals can be $C_{22}$ or smaller, $C_{16}$ or smaller, $C_{12}$ or smaller, $C_{10}$ or smaller, or $C_8$ or smaller. In many embodiments, the polyradical is divalent, trivalent, or tetravalent.

Compounds of Formula (I) feature $E^1$ that is either O or NHR' with R' being H or $C_1$ to $C_4$ alkyl. When each $E^1$ is O, the compound of Formula (I) is a compound of Formula (II). When each $E^1$ is NHR', the compound of Formula (I) is a compound of Formula (IIa).

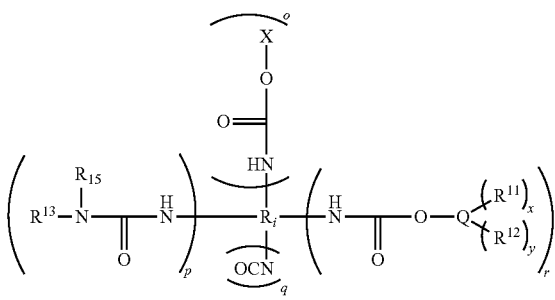

(II)

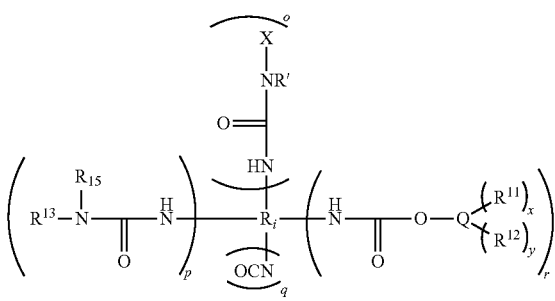

(IIa)

Compounds of Formulas (I), (II), or (IIa) can be synthesized from compounds of Formula (III).

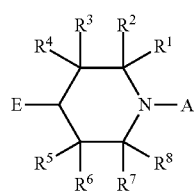

(III)

More specifically, the group $E^1$-X in the compound of Formula (I) results from the use of compounds of Formula (III) in the synthesis of compounds of Formula (I).

In the compound of Formula (III), $R^1$ through $R^8$, and A have the same meaning as in the compound of Formula (I), and E is OH or NHR', wherein R' has the same meaning as in the compound of Formula (I).

In any compound of Formula (III), $R^1$, $R^2$, $R^7$, and $R^8$ independently can be any suitable alkyl. $R^1$, $R^2$, $R^7$, and $R^8$ can be the same or different. Typical alkyls for any of $R^1$, $R^2$, $R^7$, and $R^8$ include $C_1$ or greater, $C_2$ or greater, $C_3$ or greater, $C_4$ or greater, $C_6$ or greater, $C_8$ or greater, or $C_{12}$ or greater. Other typical alkyls that can be used as one or more of $R^1$, $R^2$, $R^7$, and $R^8$ include $C_{16}$ or less, $C_{12}$ or less, $C_8$ or less, $C_6$ or less, $C_4$ or less, $C_3$ or less, or $C_2$ or less. In many cases, each of $R^1$, $R^2$, $R^7$, and $R^8$ are methyl.

$R^3$, $R^4$, $R^5$, and $R^6$ can be independently H or alkyl. When one or more of $R^3$, $R^4$, $R^5$, and $R^6$ is alkyl, the alkyl is typically $C_1$ or greater, $C_2$ or greater, $C_3$ or greater, $C_4$ or greater, $C_6$ or greater, $C_8$ or greater, or $C_{12}$ or greater. Such alkyl is often $C_{16}$ or less, $C_{12}$ or less, $C_8$ or less, $C_6$ or less, $C_4$ or less, $C_3$ or less, or $C_2$ or less. In many cases, one or more of $R^3$, $R^4$, $R^5$, and $R^6$ is H. Most commonly, each of $R^3$, $R^4$, $R^5$, and $R^6$ are H.

The identity of each of $R^1$ through $R^8$ in a compound of Formula (III) is carried over into compounds of Formula (I) that are synthesized from that compound of Formula (III). Thus, the identity of each of $R^1$ through $R^8$ in any compound of Formula (I) will depend on, and be the same as, the identity of the $R^1$ through $R^8$ in the compound or compounds of Formula (III) used as a starting material.

In some cases, E in the compound of Formula (III) is hydroxy. When such compound is employed as a starting material, the resulting compound of Formula (I) will be a compound of Formula (II). Similarly, when E is NR', the resulting compound of Formula (I) will be a compound of Formula (IIa). A can be either alkyl or oxyalkyl. When A is alkyl, then the compound of Formula (III) is a compound of, for example, Formula (IIIa). When A is oxyalkyl, then the compound of Formula (III) is a compound of, for example, Formula (IIIb).

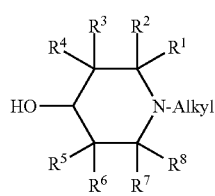

(IIIa)

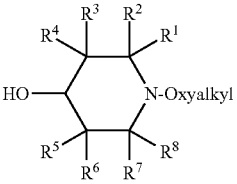

(IIIb)

The alkyl, which is attached to the ring nitrogen, in the compound of Formula (IIIa) can be any suitable alkyl. The alkyl can be linear, branched, cyclic, or a combination thereof (e.g., a cyclic alkyl that also has a linear component). Typical alkyls are $C_1$ or greater, $C_2$ or greater, $C_3$ or greater, $C_4$ or greater, $C_6$ or greater, $C_8$ or greater, or $C_{12}$ or greater. Many alkyls are $C_{16}$ or less, $C_{12}$ or less, $C_8$ or less, $C_6$ or less, $C_4$ or less, $C_3$ or less, or $C_2$ or less. In many cases, the alkyl is $C_1$ to $C_4$ alkyl. Methyl is most common.

Most commonly compounds of Formula (IIIa) feature $R^1$, $R^2$, $R^7$, and $R^8$ that are methyl, $R^3$, $R^4$, $R^5$, and $R^6$ that are H. In such cases, the compound of Formula (III) is a compound of Formula (IIIa1). The alkyl, which is connected to the nitrogen in the ring, in the compound of Formulas (IIIa) and (IIIa1) is most often methyl. In such cases, the compound of Formula (IIIa1) is a compound of Formula (IIIa2).

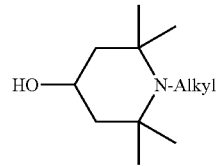

(IIIa1)

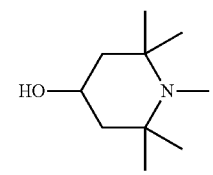

(IIIa2)

Most commonly compounds of Formula (IIIb) feature $R^1$, $R^2$, $R^7$, and $R^8$ that are methyl, and $R^3$, $R^4$, $R^5$, and $R^6$ that are H. In such cases, the compound of Formula (IIIb) is a compound of Formula (IIIb1).

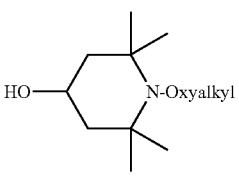

(IIIb1)

The oxyalkyl in the compound of Formula (IIIb) or (IIIb1), which is connected to the nitrogen in the ring, can be any suitable oxyalkyl. The oxyalkyl can be linear, branched, cyclic, or a combination thereof (e.g., a cyclic oxyalkyl can also have a linear component). Typical oxyalkyls are $C_1$ or greater, $C_2$ or greater, $C_3$ or greater, $C_4$ or greater, $C_6$ or greater, $C_8$ or greater, $C_{12}$ or greater, $C_{16}$ or greater, or $C_{22}$ or greater. Many oxyalkyls are $C_{26}$ or less, $C_{22}$ or less, $C_{18}$ or less, $C_{16}$ or less, $C_{12}$ or less, $C_8$ or less, $C_6$ or less, $C_4$ or less, $C_3$ or less, or $C_2$ or less. $C_8$ oxyalkyl is often used. In many cases, compounds of Formula (IIIb) or (IIIb1) contain a mixture of linear and branched isomers of the oxyalkyl group. This effect has been noted in documents that describe the preparation of such compounds, such as Schoening et al. (*J. Org. Chem.* 2009, 74, 1567-1573), U.S. Pat. No. 4,983,737, U.S. Pat. No. 5,286,865, U.S. Pat. No. 5,442,071 and US2010/0249401. Of the $C_8$ isomers, which are collectively known as oxyoctyl, branched isomers tend to occur more often than the linear isomer. When the oxyalkyl in the compound of Formula (IIIb1) is oxyoctyl, the compound of Formula (IIIb1) is a compound of Formula (IIIb2).

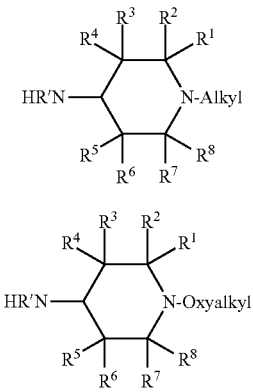
(IIIb2)

In other cases, E in the compound Formula (III) can be NHR'. When such compounds are employed as starting materials, the resulting compounds of Formula (I) will be compounds of Formula (IIa). A can be alkyl or oxyalkyl. When A is alkyl, the compound of Formula (III) is a compound of Formula (IV). When A is oxyalkyl, the compound of Formula (III) is a compound of Formula (IVa).

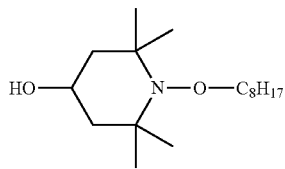
(IV)

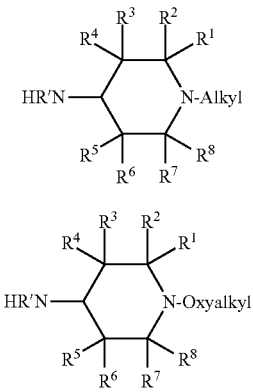
(IVa)

In compounds of Formula (IV) and (IVa), the identity of each of $R^1$ through $R^8$ is the same as in the compound of Formula (III). Most commonly, compounds of Formula (IV) feature $R^1$, $R^2$, $R^7$, and $R^8$ that are methyl, and $R^3$, $R^4$, $R^5$, and $R^6$ that are H. In such cases, the compound of Formula (IV) is a compound of Formula (IV1).

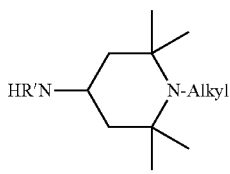
(IV1)

R' in the compound of Formula (IV) or (IV1) can be H or any $C_1$ to $C_4$ alkyl. When R' is alkyl, methyl and ethyl are most common. Typically, R' is H, in which case the compound of Formula (IV1) is a compound of Formula (IV2).

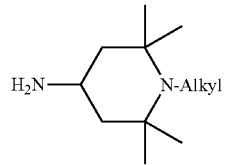
(IV2)

The alkyl, which is connected to the nitrogen in the ring, in the compound of Formula (IV), (IV1), or (IV2) can be any suitable alkyl, such as those discussed above with respect to the compound of Formulas (IIIa). Methyl is most common, in which case the compound of Formula (IV2) is a compound of Formula (IV3).

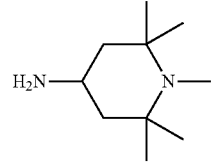
(IV3)

In the compound of Formula (IVa), the identity of each of $R^1$ through $R^8$ is the same as in the compound of Formula (III). Most commonly, compounds of Formula (IVa) feature $R^1$, $R^2$, $R^7$, and $R^8$ that are methyl, $R^3$, $R^4$, $R^5$, and $R^6$ that are H. In such cases, the compound of Formula (IVa) is a compound of Formula (IVa1).

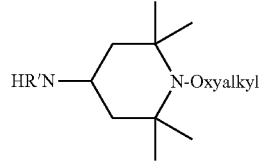
(IVa1)

R' in the compound of Formula (IVa) or (IVa1) can be H or any $C_1$ to $C_4$ alkyl. When R' is alkyl, methyl and ethyl are most common. Typically, R' is H, in which case the compound of Formula (IVa1) is a compound of Formula (IVa2).

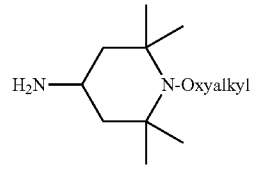
(IVa2)

In the compounds of Formulas (IVa), (IVa1), and (IVa2) the oxyalkyl, which is connected to the nitrogen in the ring, can be any suitable oxyalkyl, such as those discussed above with respect to the compound of Formula (IIIb). Oxyoctyl is most common, in which case the compound of Formula (IVa2) is a compound of Formula (IVa3).

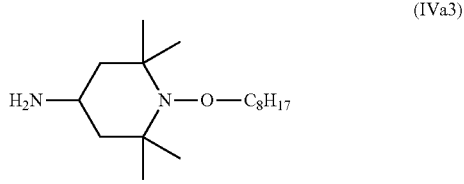

(IVa3)

The various compounds of Formula (III) discussed herein can be used in the synthesis of compounds of Formulas (I), (II), or (IIa). For example, compounds of Formula (IIIa) can be used as starting materials for compounds of Formula (I) wherein A is alkyl and $E^1$ is O, which are also compounds of Formula (II). Typically, compounds of Formula (IIIa2) are used for this purpose. Compounds of Formula (IIIa) can also be used as starting materials for compounds of Formula (II) wherein A is alkyl and $E^1$ is O. Compounds of Formula (IIIa) are sometimes known as 2,2,6,6-tetraalkyl-4-hydroxy N-alkylpiperidines, and are commercially available. Exemplary compounds of Formula (IIIa), (IIIa1), and (IIIa2) can be obtained from TCI America (OR, USA), for example, under the trade designation PMHP.

As another example, compounds of Formula (IIIb), (IIIb1), and (IIIb2) can be used as starting materials for compounds of Formula (I) wherein A is oxyalkyl and $E^1$ is O, which are also compounds of Formula (II). Compounds of Formula (IIIb) are sometimes known as alkylated N-oxyalkyl 4-hydroxy piperidines, and can be prepared from commercially available bis(alkyated N-oxyalkyl-4-piperidyl) esters of alkylene diacids as shown in Reaction Scheme 1. Exemplary bis(alkylated N-oxyalkyl-4-piperidyl) esters of alkylene diacids can be obtained from BASF (NJ, USA), for example, under the trade designation TINUVIN 123.

Compounds of Formula (IV), including compounds of Formula (IV1), (IV2), and (IV3), can be used as starting materials for compounds of Formula (I) wherein A is alkyl and $E^1$ is NR'. Compounds of Formula (IVa), including compounds of Formulas (IVa1), (IVa2), and (IVa3), can be used as starting materials for compounds of Formula (I) wherein A is oxyalkyl and $E^1$ is NR'.

Compounds of Formula (IV) and (IVa) wherein R' is H are compounds of Formula (V) and (Va), respectively. Such compounds can be synthesized from compounds of Formula (IIIa) or (IIIb), respectively, as shown in Reaction Scheme 2 and Reaction Scheme 3. First, compounds of Formulas (III) or (IIIa) can be converted to ketone intermediates of Formula (IIIb) or (IIIc) by Swern oxidation of the hydroxy group in the compounds of Formula (III) with oxalyl chloride and dimethyl sulfoxide (DMSO) followed by quenching with triethylamine. The ketone intermediates of Formula (IIIc) or (IIId) can then be converted to compounds of Formula (IV) or (IVa), respectively, by reductive amination. Reductive amination can be accomplished by any suitable procedure, such as treatment with sodium cyanoborohydride and ammonia or an amine, which is typically a protonated ammonia (an ammonium salt such as ammonium acetate) or protonated amine.

The nature of the amine used in the reductive amination reaction determines the identity of R' in the compound of Formula (IV) or (IVa). Thus, if ammonium is used, as in Reaction Scheme 2, R' in the resulting compound is H.

Reaction Scheme 1

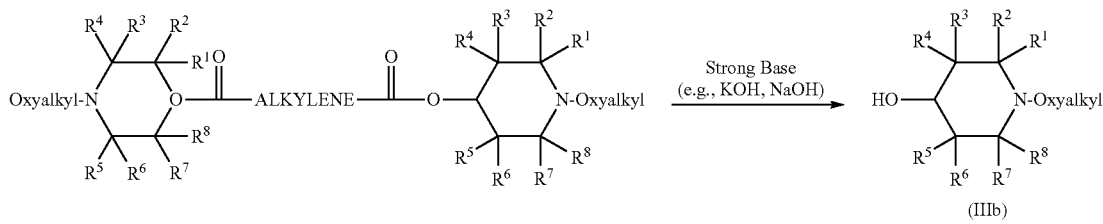

As shown in Reaction Scheme 1, treating a bis(alkylated N-oxyalkyl-4-piperidyl) ester of alkylene diacids with a strong Arrhenius base, for example an alkali metal hydroxide such as potassium hydroxide or sodium hydroxide, hydrolyzes the esters to form an alkylated N-oxyalkyl 4-hydroxy piperidine. This reaction can take place under any suitable conditions for hydrolyzing diacids. The reaction often takes place in the presence of one or more inert diluents. The one or more inert diluents are typically used to dissolve or disperse the strong Arrhenius base, the bis (alkylated N-oxyalkyl-4-piperidyl) esters of alkylene diacids, or both. Typical inert diluents include alcohols, such as methanol, ethanol, or isopropanol. The reaction can be promoted by heating. When one or more alcohols are used as the inert diluents, heating can involve refluxing the one or more alcohols. The starting material of Reaction Scheme 1 is often a bis(2,2,6,6-tetramethyl-N-oxyalkyl-4-piperidyl) ester, in which case the product of Reaction Scheme 1 is the compound of Formula (IIIb2).

Reaction Scheme 2

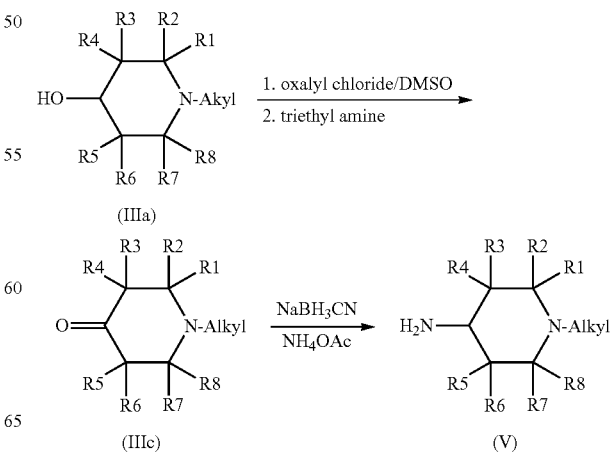

-continued
Reaction Scheme 3

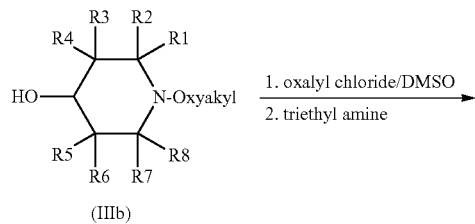

(IIIb)

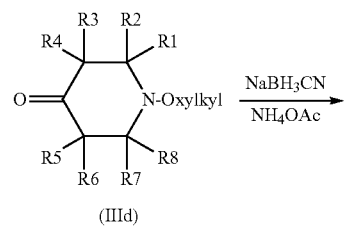

(IIId)

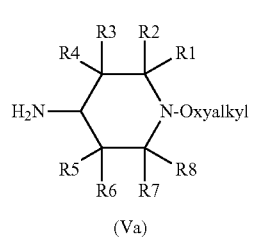

(Va)

Conditions for Swern oxidation of alcohols to ketones are known to people of ordinary skill in the art, and have been disclosed, for example, in "Oxidation of alcohols by 'activated' dimethyl sulfoxide. A preparative, steric and mechanistic study", *Tetrahedron,* 34 (11), 1978 (Omura et al.), and "Oxidation of alcohols by activated dimethyl sulfoxide and related reactions: an update", Synthesis, (10); 857-70 (Tidwell et al.). Conditions for reductive amination of carbonyls with sodium cyannoborohydride are also known to people of ordinary skill in the art, and have been disclosed, for example, in "Reductive amination with sodium cyanoborohydride: N,N-dimethylcyclohexylamine", Org. Synth. Coll., Vol. 6, 499, 1988 (Borch), and "Cyanohydriodoborate anion as a selective reducing agent", J. Am. Chem. Soc., 95 (12), 1971 (Borch et al.).

As discussed above, one method to provide compounds of Formula (IV) or (IVa) wherein R' is $C_1$ to $C_4$ alkyl is the use of a primary alkyl amine compound in the reductive amination reaction. As an alternative, compounds of Formulas (V) or (IV) can be alkylated by reaction of the primary amine with a compound of Formula (VI), as shown in Reaction Schemes 4 and 5. The resulting compounds wherein R' is $C_1$ to $C_4$ alkyl are compounds of Formula (IVb) or (IVc). The chemical structure of compounds of Formula (IVb) and (IVc) is identical whether such compounds are made by reductive amination with a primary alkyl amine in a process similar to Reaction 2 or 3 or by alkylation as shown in Reaction Schemes 4 and 5.

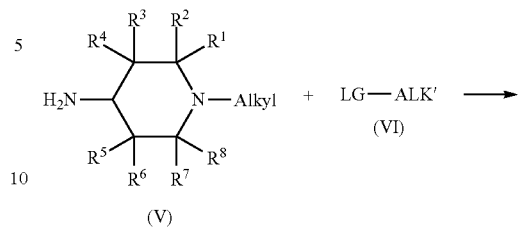

Reaction Scheme 5

In the compound of Formulas (VI), ALK' is $C_1$ to $C_4$ alkyl and LG is a leaving group. Any suitable leaving group can be used, so long as the compound of Formula (VI) is reactive with the exocyclic amine of a compound of Formulas (V) or (Va). Suitable leaving groups include halide, such as chloride, bromide, and iodide, mesylate, tosylate, and the like. Likewise, ALK' any suitable $C_1$ to $C_4$ alkyl can be used. Typical examples of $C_1$ to $C_4$ alkyl include methyl, ethyl, n-propyl, iso-propyl, and n-butyl. Methyl and ethyl are most common.

The ALK' moiety in the compounds of Formulas (IVb) and (IVc) comes from the ALK' group of compounds of Formula (VI), and is defined in the same way as that in compounds of Formula (VI).

The reactions shown in Reaction Schemes 4 and 5 can take place under any reaction conditions suitable for alkylation of a primary amine. Typically, the compound of Formula (IV) or (IVa) is first dissolved or dispersed in one or more inert diluents that do not undergo a chemical reaction under the alkylation conditions. Common inert diluents include aromatics such as benzene, toluene, and xylenes, ethers such as diethyl ether and tetrahydrofuran, as well as hydrocarbons such as hexanes. The compound of Formula (VI) can be added to the compound of Formula (V) or (Va) and the inert diluents in any suitable manner. For example, the compound of Formula (VI) can be added to the compound of Formula (V) or (Va) and the one or more inert diluents dropwise with a syringe. The reaction often takes place at ambient temperatures, but it can be facilitated by heating if necessary.

Any compound of Formulas (III), (IV), or (IVa), such as those discussed herein, can be converted into a compound of Formula (I). For example, a compound of Formula (I) can be formed by reacting any compound of Formula (III), (IV), or (IVa) with a multi isocyanate. The multi-isocyanate, which can also be referred to as a multifunctional isocyanate, typically has between 2 and 10 isocyanate groups. Multi-isocyanates that have two or three isocyanate groups are most common.

Many of the multifunctional isocyanates of greater than 2 functionality exist as a distribution of materials. For example, hexamethylene diisocyanate based isocyanate oligomers such as biuret multi-isocyanates, which are available under the trade designation DESMODUR N100, exist as a mixture of hexamethylene diisocyanate, hexamethylene diisocyanate biuret trimers, hexamethylene diisocyanate biuret pentamers, hexamethylene diisocyanate biuret heptamers, and so on. The same is true for hexamethylene diisocyanate based isocyanurate multi-isocyanates available under the trade designation DESMODUR N3300. Biuret and isocyanurate multi-isocyanates may be based on other diisocyanates such as isophorone diisocyanate, or tolylene diisocyanate. In drawing structures, below and in the Examples, only the trimers of these materials are shown; this is done for simplicity and because the trimers are believed to be the most prevalent structures in the materials as received.

Exemplary multi-isocyanates include biuret compounds of Formula (VII). In compounds of Formula (VII), G is alkylene. The identity of G is carried forward into the resulting compound of Formula (I) or (II). R' in Formula (I) is a residue of the isocyanate compound. For the compounds of Formula (VII) and (VIIa), R' is equal to the isocyanate compound minus the three isocyanato groups. As such, the identity of G in any compound of Formula (I) or (II) will depend on, and be the same as, the identities of G discussed here with respect to compounds of Formula (VII) and (VIIa).

G can be any suitable alkylene. In many cases, G is $C_1$ or greater, $C_2$ or greater, $C_3$ or greater, $C_4$ or greater, $C_6$ or greater, $C_8$ or greater, or $C_{12}$ or greater. G is often $C_{16}$ or less, $C_{12}$ or less, $C_8$ or less, or $C_6$ or less. G is most often linear, but when G is $C_3$ or greater it is possible for G to be linear, branched, cyclic, or a combination thereof (e.g., alkylene having a cyclic component and a linear component). One common G is linear $C_6$ alkylene. When G is linear $C_6$ alkylene, the compound of Formula (VII) is a compound of Formula (VIIa).

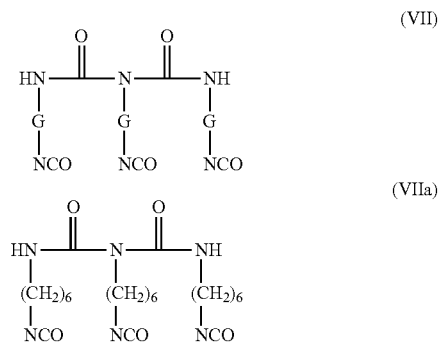

Exemplary compounds of Formula (VII) are commercially available. Exemplary compounds of Formula (VII) and (VIIa) can be obtained from Bayer Polymers LLC (Pittsburgh, USA). One such compound is obtainable under the trade designation DESMODUR N100.

Compounds of Formula (VII) or (VIIa), can react with compounds of any compound of Formula (III), including compounds of Formulas (IIIa), including (IIIa1) or (IIIa2), (IIIb), including (IIIb1) or (IIIb2), (IV), including (IV1), (IV2), or (IV3), or (IVa), including (IVa1), (IVa2), or (IVa3), to form one or more compounds of Formula (I). This reaction is shown in Reaction Scheme 6.

Compounds of Formulas (VIII), (VIIIa), (VIIIb), (VIIIc), and (VIIId) are all compounds of Formula (I) wherein $R_i$ is the HN(G)C(O)N(G)C(O)NH(G) residue of the multi-isocyanate of Formula (VIIa). Thus, the identity of G in such $R_i$ is identical to the identity of G in the compounds of Formula (VII) or (VIIa), and is often alkyl, such as $C_1$ or greater, $C_2$ or greater, $C_3$ or greater, $C_4$ or greater, $C_6$ or greater, $C_8$ or greater, or $C_{12}$ or greater. G is often $C_{16}$ or less, $C_{12}$ or less, $C_8$ or less, or $C_6$ or less. Hexyl is common. The identity of other variable elements, such as A and $E^1$, is identical to that of the compound of Formula (III) that is used in Reaction Scheme 6.

Compounds of Formulas (VIII) and (VIIIa) are compounds of Formula (I) wherein o is 1, r is 0 and q is 2, whereas compounds of Formula (VIIIb) and (VIIIc) are compounds of Formula (I) wherein o is 2, r is 0, and q is 1 and compounds of Formula (VIIIc) are compounds of Formula (I) wherein o is 3, r is 0, and q is 0. The identity of A in each of the compounds of Formulas (VIII), (VIIIa), (VIIIb), (VIIIc), and (VIIId) is identical to the identity of A in the compound of Formula (III) from which they are obtained. The identity of $E^1$ in compounds of Formulas (VIII), (VIIIa), (VIIIb), (VIIIc), and (VIIId) depends on the identity of E in the compound of Formula (III). When E in the compound of Formula (III) is NR'H, then $E^1$ in the compounds of Formulas (VIII), (VIIIa), (VIIIb), (VIIIc), and (VIIId) is NR', wherein R' is the same R' as in the compound of Formula (III). When E in the composition of Formula (III) is hydroxy, then $E^1$ in the compounds of Formulas (VIII), (VIIIa), (VIIIb), (VIIIc), and (VIIId) is O.

Reaction Scheme 6

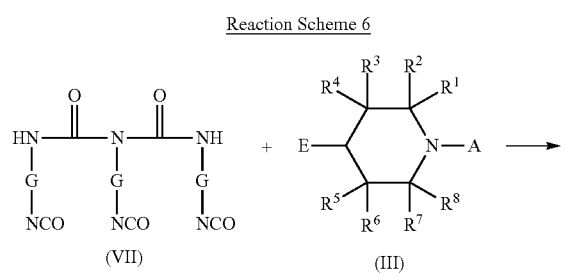

(VII)  (III)

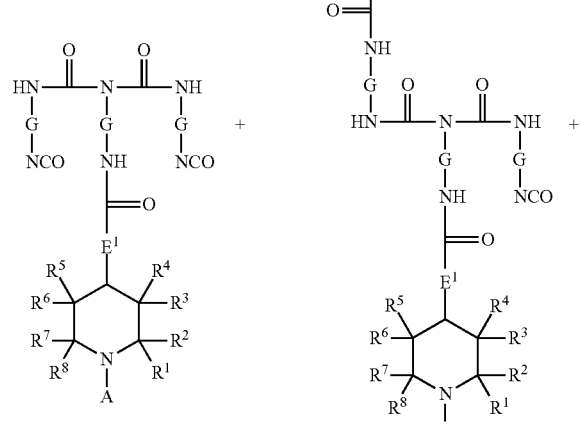

(VIII)

(VIIIa)  (VIIIb)

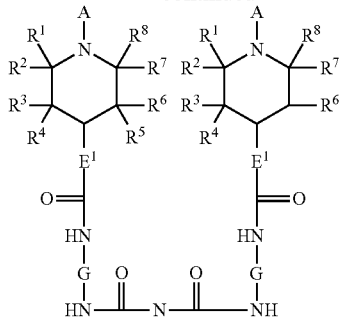

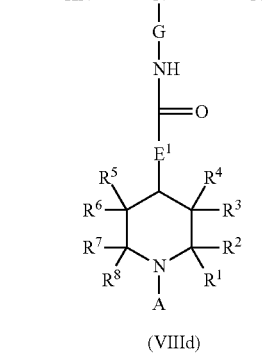

(VIIId)

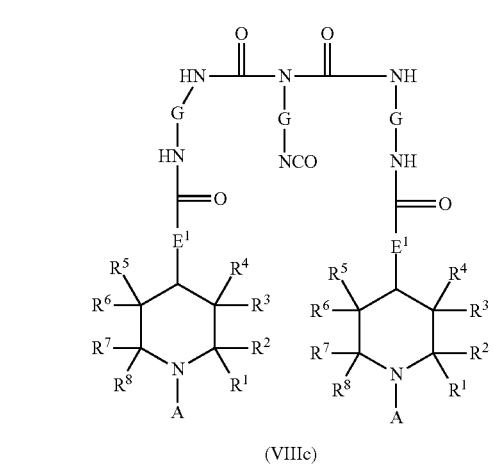

(VIIIc)

The reaction illustrated in Reaction Scheme 6 can take place under any conditions suitable for condensation of an alcohol or amine with an isocyanate. Typically, the compound of Formula (II), which is an alcohol when E is OH or an amine when E is NR'H, is admixed with the compound of Formula (VII) and (VIIa) and allowed to stir until the reaction is complete. This can take from 15 minutes to one day. An inert diluent can be used. The inert diluent is typically a liquid that dissolves or disperses one or more of the reactants but does not undergo a chemical reaction under the reaction conditions. Common inert diluents that can be used for this reaction include one or more of chlorinated compounds, such as chloroform or dichloromethane, ethers such as diethyl ether or tetrahydrofuran, and aromatic compounds, such as benzene, toluene, or xylenes.

The reaction can be facilitated by the use of a catalyst. This is particularly helpful when A in the compound of Formula (III) is oxyalkyl and E is OH; it is often not necessary when E is NR'H. Suitable catalysts include, but are not limited to tertiary amines and tin compounds. Examples of useful tin compounds include tin (II) and tin (IV) salts such as stannous octoate, dibutyl tin dilaurate, dibutyltin diacetate, dibutyltin di-2-ethylexanoate, and dibutyltin oxide. Examples of tertiary amines include triethyl amine, tributyl amine, triethylenediamines, tripropylamine, bis(dimethylamineoethyl)ether, morpholine compounds such as ethyl morpholine, and 2,2-dimorpholinodiethyl ether, 1,4-diazobicyclo[2.2.2]octane (available from Aldrich Chemical Co., Milwaukee, Wis., USA, under the trade designation DABCO), and 1,8-diazobicyclo[5.4.0]undec-7-ene (available from Aldrich Chemical Co., Milwaukee, Wis., USA, under the trade designation DBU). Tin compounds are most common, and are commonly used in levels from 50 to 100,000 parts per million (ppm) based on the total solids in the reaction, with a level of 100 to 1,000 ppm being typical. When an amine catalyst is used, it is typically used in levels from 0.01 to 1.00 mol equivalents based on the mol equivalents of alcohol in the reaction. In some cases, both a tin catalyst and an amine catalyst can be used.

The reaction of a compound of Formula (III) with a compound of Formula (VII) or (VIIa) provides a plurality of products, because group E in the compound of Formula (III) can react with one or more of the isocyanate moieties on the compound of Formula (VII) or (VIIa). The products of Reaction Scheme 6 are a mixture of compounds of Formula (I) wherein o is 1, 2, or 3, depending on whether the residue of the multi-isocyanate of Formula (VIIa) is mono, di, or tri substituted (depending on the number of unreacted isocyanato groups). The degree of substitution can be influenced by changing the stoichiometric ratio of the compound of Formula (III) and the compound of Formula (VII) or (VIIa). Using one equivalent or less of the compound of Formula (III), with respect to the number of isocyanate moieties in the compound of Formula (VII) or (VIIa), favors the formation of the mono-substituted compounds of Formulas (VIII) and (VIIIa). Using three equivalents or more of the compound of Formula (III), with respect to the number of isocyanate moieties in the compound of Formula (VII) or (VIIa), favors the formation of the tri-substituted compound of Formula (VIIIc). In most cases, however, the result of the reaction of a compound of Formula (III) with a compound of Formula (VII) or (VIIa) is a mixture of compounds of Formulas (VIII), (VIIIa), (VIIIb), and (VIIIc).

Compounds of Formula (VIII), (VIIIa), (VIIIb), or (VIIIc) can be converted to compounds of Formula (I), (II), or (IIa), by attaching one or more silyl groups. Compounds of Formula (VIIId) have no reactive isocyanate groups remaining for attachment of one or more silyl groups, and therefore cannot be converted to a compound of Formula (I).

G in the compounds of Formulas (VIII), (VIIIa), (VIIIb), and (VIIIc) is typically hydrocarbon polyradical, particularly $C_1$ to $C_{12}$ or $C_1$ to $C_6$ hydrocarbon polyradical. The hydrocarbon polyradical is often alkylene (alkane-diyl), alkane-triyl, or alkane-tetrayl. The hydrocarbon polyradical is often $C_1$ to $C_{12}$ or $C_1$ to $C_6$ alkylene. Hexylene is most common.

A in the compounds of Formulas (VIII), (VIIIa), (VIIIb), (VIIIc) and can be alkyl or oxyalkyl. When alkyl is employed, the alkyl is typically $C_1$ to $C_{12}$ alkyl, such as $C_1$ to $C_6$ alkyl. Methyl is most common. When oxyalkyl is employed, the oxyalkyl is typically $C_1$ to $C_{12}$ oxyalkyl. Oxyoctyl is most common.

There are two approaches to attaching one or more silyl groups to compounds of Formula (VIII), (VIIIa), (VIIIb), and (VIIIc). These two approaches can be used separately or in combination. The first approach begins by converting a compound of Formula (VIII), (VIIIa), or (VIIIb) to an (alkyl)acrylate intermediate. Such conversion can be accomplished by any suitable chemical transformation. Typically, an isocyanate group in a compound of Formula (VIII), (VIIIa), or (VIIIb) is reacted with a hydroxy-containing acrylate or multi-acrylate, such as a compound of Formula (IX).

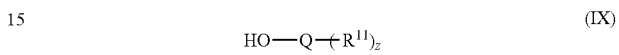
(IX)

In Formula (IX), Q is a connecting group and each $R^{11}$ is independently an (alkyl)acryloyloxy or, more specifically a (meth)acrylolyoxy functional group of the formula $OC(O)C(R^d)=CH_2$. The variable z is the number of $R^{11}$ groups attached to Q, which can be from 1 to 6.

Q can be any suitable connecting group, such as hydrocarbon polyradical, alkylene, alkenylene, alkynylene, alkyleneoxyalkylene, alkyleneneaminoalkylene, and the like. For example Q can be a linear, branched, or cycle-containing connecting group. Q can include a covalent bond, alkylene, arylene, or aralkylene. Q can optionally include heteroatoms, most often one or more of O, N and S. Q can also optionally include heteroatom containing functional groups, such as carbonyl, sulfonyl, or both.

Q is most commonly hydrocarbon polyradical or alkylene. Hydrocarbon polyradical is most common when z is greater than 1. Common hydrocarbon polyradicals include $C_1$ to $C_{12}$ hydrocarbon polyradical, such as $C_1$ to $C_6$ hydrocarbon polyradical. Q is typically alkylene when z is 1. Common alkylenes include $C_1$ to $C_{12}$ alkylene, such as $C_1$ to $C_6$ alkylene, for example ethylene, propylene, butylene, and the like. In most cases, z is 1 to 3, with 1 and 3 being most common.

The identity of z, Q, and $R^{11}$, including $R^d$, in compounds of Formula (IX) carry over into any compound that is prepared from a compound of Formula (IX). Thus, any compound that can be prepared from a compound of Formula (IX), such as any compound of Formula (I) having an r of 1 or greater, will have a z, Q, and ACRYL (which refers to an (alkyl)acryloyloxy such as (meth)acryloyloxy), including $R^d$, with identities that are the same as that discussed above with respect to compounds of Formula (IX).

Many compounds of Formula (IX) are commercially available. Exemplary compounds of Formula (IX) wherein z is 1 include of hydroxyalkyl (meth)acrylates, such as 2-hydroxyethyl acrylate, methyl 2-(2-hydroxy-1-methylethyl)acrylate, and methyl 2-(2-hydroxy-1-phenylethyl) acrylate, all of which are available from Sigma-Aldrich (Milwaukee, USA). Exemplary compounds of Formula (IX) wherein p is greater than 1 include pentaerythritol triacrylate which is available from Sartomer Company (Exton, Pa., USA) under the trade designation SR444C, and 3-(acryloxy)-2-hydroxypropyl methacrylate (CAS number 1709-71-3) available from Sigma-Aldrich (Milwaukee, Wis., USA).

Compounds of Formula (IX) can react with compounds of Formulas (VIII), (VIIIa), (VIIIb), or (VIIIc) under any condition suitable for reaction of a hydroxyl group with an isocyanate. In many cases, the reaction can be conducted at ambient temperature by stirring the compound of Formula (IX) with a compound of Formula (VIII), (VIIIa), (VIIIb), or (VIIIc) in one or more inert diluents. Typical inert diluents do not undergo chemical reactions under the reaction conditions, and include aromatics such as benzene and toluene, ethers such as diethyl ether and tetrahydrofuran, and chlorinated diluents such as dichloromethane and chloroform. The reaction can often take place at ambient temperatures; however, the reaction can be facilitated by heating, for example, to approximately 60° C.

Reaction Scheme 7 provides an example of this conversion by illustrating the reaction of a compound of Formula (VIII) with a compound of Formula (IX).

The reaction results in a mixture of products, which are compounds of Formulas (X), (Xa), and (Xb). Compounds of Formula (X) and (Xa) feature one O-Q-$(R^{11})_z$ group and one isocyanate group per molecule. Some control over the relative amount of the reaction products can be achieved by varying the amount of the compound of Formula (IX) that is used in the reaction. Using less than one equivalent of the compound of Formula (IX) will favor the formation of compounds of Formulas (X) and (Xa), whereas using more than two equivalents will favor the formation of the compound of Formula (Xb).

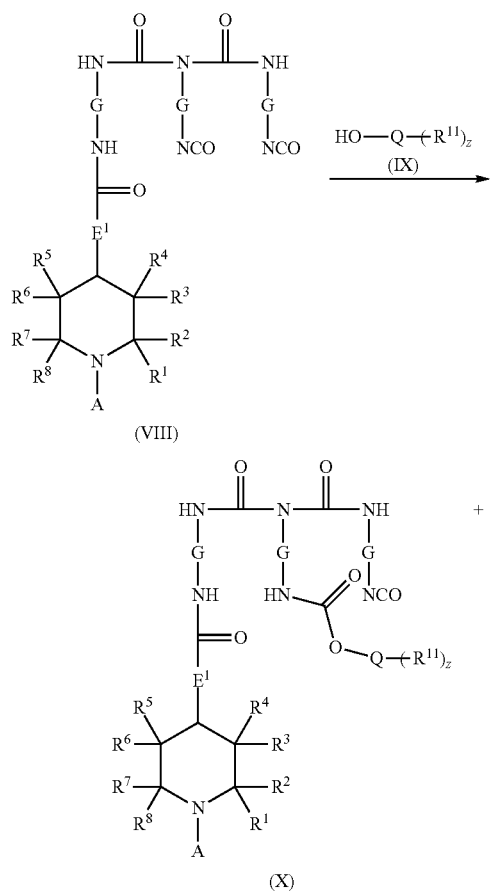

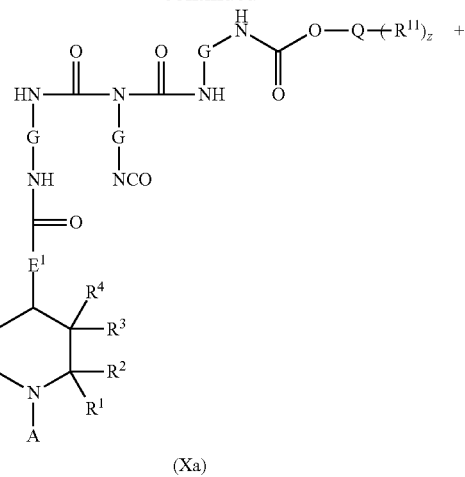

(Xa)

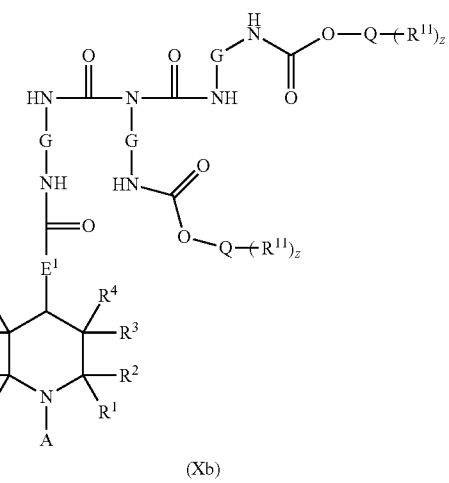

(Xb)

In compounds of Formulas (X), (Xa), and (Xb), the identity of A, $R^1$ through $R^8$, $E^1$, and each G is carried over from the compound of Formula (VIII). Thus, the identity of any of these elements is the same as that described above with respect to Formula (VIII). Similarly, the identity of Q is carried over from the compound of Formula (IX), and is therefore the same as that described above with respect to the compound of Formula (IX). $R^{11}$ in these compounds typically feature an $R^d$ that is methyl or H.

The products of Reaction Scheme 7, compounds of Formulas (X), (Xa), and (Xb), can be converted to compounds of Formula (I) by reacting the carbon-carbon double bond of one or more $R^{11}$ groups with a compound of Formula (XI).

(XI)

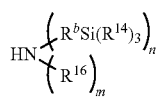

The compound of Formula (XI) is an aminoalkylsilyl compound or an amino-bis(alkylsilyl) compound. The number of $R^b$ $Si(R^{14})$ groups bound to the nitrogen atom is represented by n, which is 1 or 2. In such groups, $R^b$ is alkylene, typically a $C_1$ to $C_{12}$ alkylene such as $C_1$ to $C_6$ alkylene. Each $R^{14}$ is independently OH, oxyalkyl, OC(O)$R^d$ or alkyl; at least one $R^{14}$ is OH, OC(O)$R^d$, or oxyalkyl, since those groups are needed to affix the compound to a substrate, such as a glass or ceramic substrate. When oxyalkyl is used, it is typically $C_1$ to $C_4$ oxyalkyl. Oxyethyl and oxymethyl are most common. When alkyl is used, it is typically $C_1$ to $C_4$ alkyl, such as ethyl or methyl. In many cases, each $R^{14}$ is oxyalkyl, such as oxymethyl or oxymethyl. When one or more $R^{14}$ moieties are OC(O)$R^d$, $R^d$ can be H but is more commonly $C_1$ to $C_6$ alkyl. Methyl and ethyl are commonly used, with methyl being most common. The number of $R^{16}$ groups bound to the nitrogen atom is represented by m, which is 0 or 1. The sum of n+m is equal to 2. $R^{16}$ is defined as above with respect to Formula (I). When present (that is, when m is 1), $R^{16}$ is most commonly alkyl, typically $C_1$ to $C_6$ alkyl.

Many compounds of Formula (XI) are known in the art and are commercially available. For example, bis-(3-trimethoxysilylpropyl)amine is obtainable from Evonik Corp. (Piscataway, N.J., USA) under the trade designation DYNASLAN 1124 and from Momentive Co. (Huntersville, N.C., USA) under the trade designation SILQUEST 1170. In addition, 3-aminopropyltriethoxysilane (DYNASYLAN AMEO), 3-aminopropylmethyldiethoxysilane (DYNASYLAN 1505), 3-aminopropyltrimethoxysilane (DYNASYLAN AMMO), bis-(3-triethoxysilylpropyl)amine (DYNASYLAN 1122), and bis-(3-trimethoxysilylpropyl)amine (DYNASYLAN 1124) are each obtainable from Evonik Corp. (Piscataway, N.J., USA) under the indicated trade designations. Also, N-methylaminopropyltrimethoxysilane is available from Gelest (Morrisville, Pa., USA) under the trade designation SIM6500.0-25 GM.

A compound of Formula (I) can be formed by reaction of a compound of Formula (XI) with, for example, a compound of Formula (X), (Xa), or (Xb). Specifically, the compound of Formula (XI) can add across the carbon-carbon double bond of $R^{11}$ in a compound of Formula (X), (Xa), or (Xb) to form an adduct. This reaction can take place under any suitable reaction conditions. Typically, a compound of Formula (XI) is admixed with a compound of Formula (X), (Xa), or (Xb) and an inert diluent. The inert diluent is typically a liquid that dissolves or disperses one or both of the reactants and does not undergo chemical reaction under the reaction conditions. Exemplary inert diluents include ether such as diethyl ether, ethyl t-butyl ether, and tetrahydrofuran, chlorinated compounds such as chloroform and dichloromethane, aromatic compounds such as benzene, toluene, and xylenes, carbonyl compounds such as acetone and methyl ethyl ketone, ethers such as ethyl acetate, and aliphatic hydrocarbons such as hexanes. The reactants and inert diluent can be stirred for a time sufficient to complete the reaction, which is typically from 15 minutes to 12 hours, and often from 30 minutes to 2 hours.

An exemplary reaction of this type is illustrated in Reaction Scheme 8, which depicts a reaction between a compound of Formula (Xb) and a compound of Formula (XI).

Reaction Scheme 8

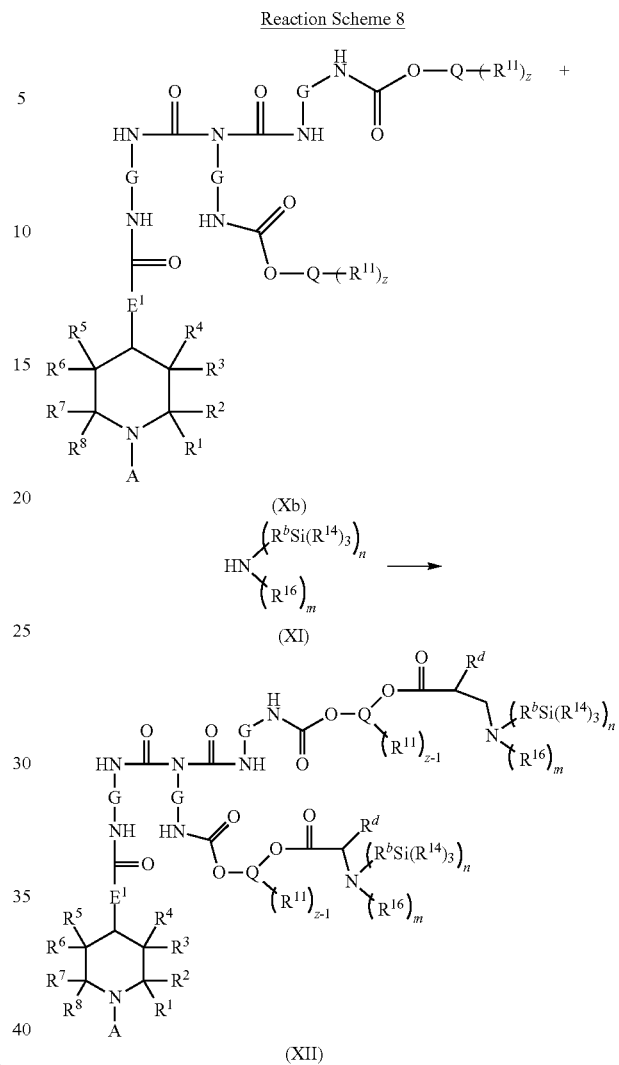

The reaction depicted in Reaction Scheme 8 can take place under any conditions suitable for addition of an amine to the carbon-carbon double bond in $R^{11}$ moieties. Typically, the compound of formula (Xb) is heated to a temperature that facilitates the reaction, such as from 40° C. to 80° C., and the compound of Formula (XI) is then added. Addition of the compound of Formula (XI) can take place in a dropwise manner. The reactants are typically stirred at the elevated temperature for sufficient time for the reaction to complete, which is usually no less than 20 minutes and no more than one day after addition of the compound of Formula (XI) is complete. The progress of the reaction can be monitored by conventional techniques, such as thin layer chromatography, for the disappearance of the compound of Formula (Xb), and can be complete when that compound is no longer available. The reaction often takes place in the presence of an inert diluent. The diluent, when used, is typically one or more liquids that do not undergo a chemical transformation under the reaction conditions. Exemplary inert diluents include chlorinated hydrocarbon such as chloroform and methylene chloride, aromatic compounds such as benzene, toluene, and xylenes, and ether such as tetrahydrofuran, diethyl ether, and methyl butyl ether. In many cases, the reaction proceeds under a dry atmosphere. Conducting chemical reactions under dry atmosphere is a technique well known to the person of ordinary skill in the art.

The product of Reaction Scheme 8 is a compound of Formula (XII). Compounds of Formula (XII) are compounds of Formula (I) wherein o is 1, r is 2, z is 0 and p is 0. $R^{12}$ in the compound of Formula (I) is drawn as —OC(O)CH($R^d$)CH$_2$N($R^{16}$)$_x$($R^b R^{14}$)$_y$ in the depiction of compound of Formula (XII). Thus, the identity of $R^d$, $R^{16}$, $R^b$, $R^{14}$, x, and y are the same as defined above with respect to compounds of Formula (I). In most cases, $R^d$ is H, since the addition of the amine is much more facile in this case than when $R^d$ is alkyl. $R^{16}$ is often $R^{13}$. In some cases, $R^{16}$ is H. When $R^{16}$ is alkyl, it is typically no larger than $C_{12}$ alkyl or no larger than $C_6$ alkyl. $C_1$ to $C_6$ alkyl are most common, particularly methyl, ethyl propyl, butyl, or cyclohexyl.

The second approach to forming compounds of Formula (I) involves condensing the compound of Formula (XIa) directly with one or more isocyanate groups of a HALS or NORHALS substituted multi-isocyanate. This reaction can take place under any conditions suitable for such condensation, such as those described above with respect to the reaction of compounds of Formula (III) and (IV) with multi-isocyanates. An exemplary reaction of this type is illustrated in Reaction Scheme 9.

Reaction Scheme 9

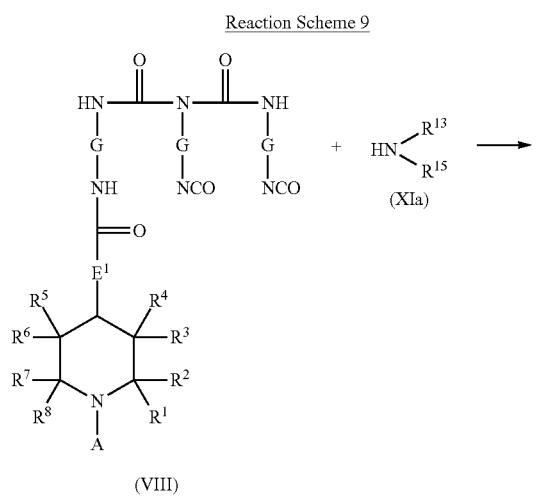

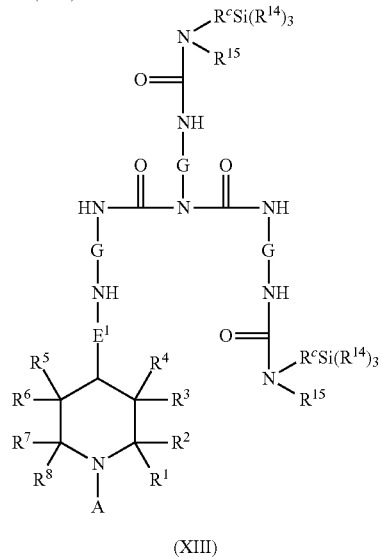

(XIII)

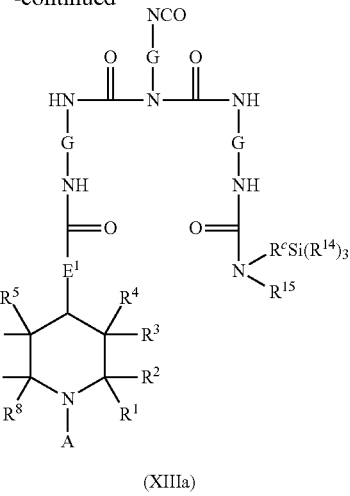

(XIIIa)

The reaction of Reaction Scheme 9 can take place under any conditions suitable for condensation of an amine with an isocyanate. Such conditions are known to the person of skill in the art, and have also been described above with respect to Reaction Scheme 6.

In the compound of Formula (XIa), used in reaction Scheme 9, $R^{13}$ is $R^c$Si($R^{14}$)$_3$, wherein $R^{14}$ is defined as described above with respect to the compound of Formula (XI). $R^c$ can be alkylene, alkylene amine alkylene, or alkylene amine alkylene amine alkylene. When $R^c$ is alkylene, it can be any suitable alkylene, typically $C_1$ to $C_{12}$, such as $C_1$ to $C_6$ or $C_1$ to $C_4$ alkylene. When $R^c$ is alkylene amine alkylene, each of the two alkylene moieties can independently be any suitable alkylene; typically both are $C_1$ to $C_{12}$, such as $C_1$ to $C_6$ or $C_1$ to $C_4$ alkylene. When $R^c$ is alkylene amine alkylene amine alkylene, each of the three alkylene moieties can independently be any suitable alkylene; typically each are $C_1$ to $C_{12}$, such as $C_1$ to $C_6$ or $C_1$ to $C_4$ alkylene.

$R^{15}$ is $R^{13}$, H or, alkyl. When $R^{15}$ is $R^{13}$, it is defined as discussed above. When $R^{15}$ is alkyl, it can be any suitable alkyl but is typically $C_1$ to $C_{12}$, such as $C_1$ to $C_6$ or $C_1$ to $C_4$ alkyl. $R^{15}$ can also be H.

Many compounds of Formula (XIa) are known in the art and are commercially available such as, for example, 3-aminopropyltriethoxysilane (DYNASYLAN AMEO), 3-aminopropylmethyldiethoxysilane (DYNASYLAN 1505), 3-aminopropyltrimethoxysilane (DYNASYLAN AMMO), H$_2$NCH$_2$CH$_2$NH—(CH$_2$)$_3$—NH—(CH$_2$)$_3$—Si(OCH$_3$)$_3$ (DYNASYLAN TRIAMO), N-(n-butyl)-3-aminopropyltrimethoxysilane (DYNASYLAN 1189), 2-aminoethyl-3-aminopropyltrimethoxysilane (DYNASYLAN DAMO), bis-(3-triethoxysilylpropyl)amine (DYNASYLAN 1122), and bis-(3-trimethoxysilylpropyl)amine (DYNASYLAN 1124) which are all obtainable from Evonik Corp. (Piscataway, N.J., USA) under the DYNASYLAN trade designation. Also, N-methylaminopropyltrimethoxysilane is available from Gelest (Morrisville, Pa., USA) under the trade designation SIM6500.0.

The product of Reaction Scheme 9 are compounds of Formula (XIII) and (XIIIa). The compound of Formula (XIIIa) exists as two regioisomers, wherein the isocyanato moiety can be attached at terminal —NHG group or an interior —NHG group; for simplicity only the latter is shown.

Compounds of Formula (XIII) are compounds of Formula (I) wherein o is 1, r and q are each 0, and p is 2, whereas compounds of Formula (XIIIa) are compounds of Formula (I) wherein o is 1, q is 1, r is 0, and p is 1. While Reaction Scheme 9 can be a mixture of these products, the compound of Formula (XIII) can be favored by using two equivalents, or slightly more, of the compound of Formula (XI), whereas the compound of Formula (XIIIa) can be favored by using one equivalent, or slightly less, of the compound of Formula (XI).

The identity of $R^{13}$, including all sub-elements thereof, in the resulting compound of Formula (I) corresponds to the identity of the particular compound of Formula (XIa) that is employed in Reaction Scheme 9; specifically, the identity of $R^{13}$ is identical to that of the compound of Formula (XIa), except that one nitrogen-bound H atom in the compound of Formula (XIa) is no longer present in $R^{13}$. As an aid in understanding the structures, the depiction of the compounds of Formulas (XIII) and (XIIIa) in Reaction Scheme 9 shows $R^{13}$ as $R^e Si(R^{14})_3$. The remaining variables in the compound of Formula (XIII) are defined in the same manner as discussed above with respect to compounds of Formula (XIa) or (VIII), and are identical to those in the particular compounds of Formulas (XIa) and (VIII) that are used in Reaction Scheme 9.

The two approaches to covalently bonding silyl groups to the multi-isocyanate described above can be used separately or in conjunction with one another. Thus, a compound of Formula (I) wherein p and r are both for greater can be formed by first chemically reacting a HALS or NORHALS functionalized multi-isocyanate with a compound of Formula (IX) such that some of the isocyanate moieties in the multi-isocyanate are still free. An example of this is the compound of Formula (X); a method of making this compound is shown in Reaction Scheme 7. Second, the resulting compound can be chemically reacted with a compound of Formula (XIa) to form silyl groups that are bound to the multi-isocyanate both by direct condensation with one or more isocyanate moieties and by condensation with one or more acrylate groups. If the stoichiometry of the reaction is controlled such that some of the isocyanate moieties in the multi-isocyanate remain unreacted at the end of this reaction, then the resulting compound of Formula (I) will also feature q that is 1 or greater.

The illustrations provided thus far focus on the use of particular multi-isocyanates, which provide particular identities for $R_i$ in the resulting compound of Formula (I). However, the nature of $R_i$ is not limited to the residues of multi-isocyanates illustrated above. Because the reactive chemical moieties are the same regardless of the identity of the multi-isocyanate, a person of skill in the art can carry out the chemical reactions using the guidance provided herein, particularly with respect to Reaction Schemes 6, 7, 8, and 9. The identity of $R_i$ in any resulting compound of Formula (I) will depend on the specific isocyanate used.

Any multi-isocyanate can be used in the same manner as those discussed above. For example, di-isocyanates can be used in which case o+p+q+r will equal 2 in the resulting compound of Formula (I). Exemplary multi-isocyanates that can be used include those discussed in U.S. Pat. No. 7,718,264 at column 8, lines 10-26, and compounds of Formulas (XIV), (XV), (XVI), and (XVII), all of which are commercially available. For example, the compound of Formulas (XIV), (XV), (XVI), and (XVII), are obtainable under the trade designation DESMODUR N3600 (XIV), DESMODUR N3900 (XV), DESMODUR N3400 (XVI), and DESMODUR W (XVII), respectively, all of which are available from Bayer Polymers LLC (Pittsburgh, USA).

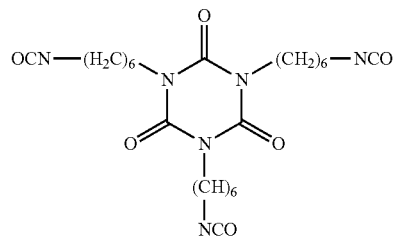

(XIV)

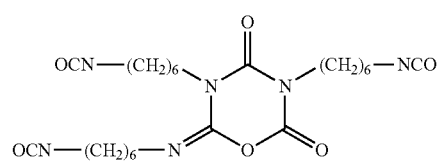

(XV)

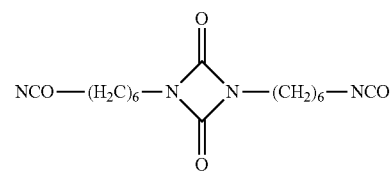

(XVI)

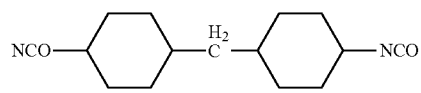

(XIV)

All of the compounds described herein have one or more silyl groups featuring a silicon atom with at least one covalent bond to a hydroxyl group or an oxyalkyl group. Such moieties allow the compounds to be affixed to a variety of surfaces, such as glass or ceramic surfaces, as well as the surfaces of nanoparticles such as silica nanoparticles. Techniques for affixing molecules containing such silyl groups to glass or ceramic surfaces, or to silica nanoparticles, are known in the art. Once affixed, compounds of Formula (I) can mitigate the negative effects of actinic radiation, such as visible and UV light, on the surface, by way of the HALS or NORHALS moieties.

Silica nanoparticles having one or more compounds of Formula (I) affixed thereto can be added to polymers, such as urethanes, acrylates, and others. The resulting compositions contain HALS or NORHALS moieties that can mitigate the negative effects of actinic radiation, such as visible and UV light, on the composition.

List of Exemplary Embodiments

The following list of embodiments is intended to better illustrate particular aspects of the disclosure. None of the embodiments enumerated below is intended to be limiting, unless otherwise specified.

Embodiment 1 is a compound having the structure of Formula (I):

$$\left( R^{13}-N-\underset{O}{\overset{R^{15}}{\underset{|}{N}}}-\underset{H}{N}-\right)_p \left( R_i \overset{X}{\underset{\underset{HN}{\overset{O}{\|}}}{\underset{|}{E^1}}} \right)_o (OCN)_q \left( \underset{H}{N}-\underset{O}{\overset{O}{\|}}-O-Q\underset{R^{12}}{\overset{R^{11}}{\underset{y}{\overset{x}{\bigg\langle}}}} \right)_r \tag{I}$$

wherein $R_i$ is a residue of a multi-isocyanate;
$E^1$ is O or NR';
R' is H or $C_1$ to $C_4$ alkyl;
X is $R^1$ is alkyl;
$R^2$ is alkyl;
$R^3$ is H or alkyl;
$R^4$ is H or alkyl;
$R^5$ is H or alkyl;
$R^6$ is H or alkyl;
$R^7$ is alkyl;
$R^8$ is alkyl;
A is alkyl or oxyalkyl;
o is the number of $NHC(O)E^1X$ groups bound to $R_i$, which is between 1 and 9;
each Q is independently a connecting group having a valence of x+y+1;
each $R^{11}$ is independently an (alkyl)acrylolyoxy functional group of the formula $OC(O)C(R^d)=CH_2$, wherein each $R^d$ is independently alkyl or H;
x is the number of $R^{11}$ groups attached to a Q, which is from 0 to 6;
y is the number of $R^{12}$ groups attached to a Q, which is from 0 to 6;
each $R^{12}$ is independently $-OC(O)CH(R^d)CH_2-R^a$ wherein $R^d$ is defined as above;
$R^a$ is $N(R^{16})_m(R^bSi(R^{14})_3)_n$;
$R^{16}$ is alkyl;
$R^b$ is alkylene that is also bound to the Si atom of $Si(R^{14})_3$;
each $R^{14}$ is independently selected from alkyl, oxyalkyl, $OC(O)R^d$, and hydroxyl, with the proviso that at least one $R^{14}$ is oxyalkyl, $OC(O)R^d$, or hydroxyl;
m is the number of $R^{16}$ groups bound to N, which is 0-1;
n is the number of $R^b$ groups bound to N, which is 1 or 2;
r is the number of $$HN-\underset{O}{\overset{O}{\|}}-O-Q\underset{R^{12}}{\overset{R^{11}}{\underset{y}{\overset{x}{\bigg\langle}}}}$$

groups attached to $R_i$, which is from 0 to 6;
each $R^{13}$ is independently $R^cSi(R^{14})_3$;
each $R^c$ is independently alkylene, alkylene amine alkylene, or alkylene amine alkylene amine alkylene that is also bound to the Si atom of $Si(R^{14})_3$;
each $R^{15}$ is independently $R^{13}$, H, or alkyl;
p is the number of $R^{13}(R^{15})NC(O)NH$ groups bound to $R_i$, which is from 0 to 9;
q is the number of NCO groups covalently bound to $R_i$, which is from 0 to 8;
with the proviso that the sum of p+q+o+r is from 2 to 10;
with the proviso that the sum of p and y is at least 1; and
with the proviso that when p is 0, x and y are both 0.

Embodiment 2 is a compound of embodiment 1 having the structure of Formula (II).

Embodiment 3 is a compound of embodiment 1 having the structure of Formula (IIa).

Embodiment 4 is a compound of any of the preceding embodiments wherein A is alkyl.

Embodiment 5 is a compound of embodiment 4 wherein A is $C_1$ to $C_{12}$ alkyl.

Embodiment 6 is a compound of embodiment 5 wherein A is $C_1$ to $C_6$ alkyl.

Embodiment 7 is a compound of embodiment 6 wherein A is methyl.

Embodiment 8 is a compound of any of embodiments 1-3 wherein A is oxyalkyl.

Embodiment 9 is a compound of embodiment 8 wherein A is $C_1$ to $C_{12}$ oxyalkyl.

Embodiment 10 is a compound of embodiment 9 wherein A is $C_8$ oxyalkyl.

Embodiment 11 is a compound of any of the preceding embodiments wherein $R^1$ is $C_1$ to $C_6$ alkyl.

Embodiment 12 is a compound of embodiment 11 wherein $R^1$ is methyl.

Embodiment 13 is a compound of any of the preceding embodiments wherein $R^2$ is $C_1$ to $C_6$ alkyl.

Embodiment 14 is a compound of embodiment 13 wherein $R^2$ is methyl.

Embodiment 15 is a compound of any of the preceding embodiments wherein $R^3$ is H.

Embodiment 16 is a compound of any of the preceding embodiments wherein $R^4$ is H.

Embodiment 17 is a compound of any of the preceding embodiments wherein $R^5$ is H.

Embodiment 18 is a compound of any of the preceding embodiments wherein $R^6$ is H.

Embodiment 19 is a compound of any of the preceding embodiments wherein $R^7$ is $C_1$ to $C_6$ alkyl.

Embodiment 20 is a compound of embodiment 19 wherein $R^7$ is methyl.

Embodiment 21 is a compound of any of the preceding embodiments wherein $R^8$ is $C_1$ to $C_6$ alkyl.

Embodiment 22 is a compound of any of embodiment 21 wherein $R^8$ is methyl.

Embodiment 22a is a compound of any of the preceding embodiments wherein A is alkyl.

Embodiment 23 is a compound of embodiment 22a wherein the alkyl is $C_1$ to $C_{12}$ alkyl.

Embodiment 24 is a compound of embodiment 23 wherein the alkyl is $C_1$ to $C_6$ alkyl.

Embodiment 25 is a compound of embodiment 24 wherein the alkyl is methyl.

Embodiment 25a is a compound of any of embodiments 1-22 wherein A is oxyalkyl.

Embodiment 26 is a compound of embodiment 25a wherein the oxyalkyl is $C_1$ to $C_{12}$ oxyalkyl.

Embodiment 27 is a compound of embodiment 26 wherein the oxyalkyl is oxyoctyl.

Embodiment 28 is a compound of any of the preceding embodiments wherein $E^1$ is O.

Embodiment 29 is a compound of any of embodiments 1-27 wherein $E^1$ is NR'.

Embodiment 30 is a compound of embodiment 28 wherein R' is H.

Embodiment 31 is a compound of embodiment 29 wherein R' is $C_1$ to $C_4$ alkyl.

Embodiment 32 is a compound of any of the preceding embodiments wherein o is 1 to 6.

Embodiment 33 is a compound of any of the preceding embodiments wherein o is 1 to 3.

Embodiment 34 is a compound of any of the preceding embodiments wherein o is 1 to 2.

Embodiment 34a is a compound of any of the preceding embodiments wherein o is 1.

Embodiment 35 is a compound of any of the preceding embodiments wherein q is 0 to 6.

Embodiment 36 is a compound of any of the preceding embodiments wherein q is 0 to 3.

Embodiment 37 is a compound of any of the preceding embodiments wherein q is 0 to 2.

Embodiment 38 is a compound of any of the preceding embodiments wherein q is 0.

Embodiment 39 is a compound of any of the preceding embodiments wherein $R^{13}$ is $R^c Si(R^{14})_3$, and $R^c$ is $C_1$ to $C_{12}$ alkylene.

Embodiment 40 is a compound of embodiment 39 wherein $R^c$ is $C_1$ to $C_6$ alkylene.

Embodiment 41 is a compound of any of the preceding embodiments, wherein $R^{13}$ is $R^c Si(R^{14})_3$, and each $R^{14}$ is independently selected from oxyalkyl, $OC(O)R^d$, and hydroxyl.

Embodiment 42 is a compound of embodiment 41 wherein at least one $R^{14}$ is oxyalkyl.

Embodiment 43 is a compound of embodiment 42 wherein each $R^{14}$ is oxyalkyl.

Embodiment 44 is a compound of embodiment 41 wherein at least one $R^{14}$ is hydroxyl.

Embodiment 45 is a compound of any of embodiments 41-44 wherein the oxyalkyl is $C_1$ to $C_6$ oxyalkyl.

Embodiment 46 is a compound of embodiment 45 wherein the oxyalkyl is methyl or ethyl.

Embodiment 47 is a compound of any of the preceding embodiments wherein p is 1 to 6.

Embodiment 48 is a compound of any of the preceding embodiments wherein p is 1 to 3.

Embodiment 49 is a compound of any of the preceding embodiments wherein p is 1 to 2.

Embodiment 50 is a compound of any of embodiments 1-46 wherein p is 0, r is at least 1, and y is at least 1.

Embodiment 51 is a compound of any of the preceding embodiments wherein Q is hydrocarbon polyradical.

Embodiment 52 is a compound of embodiment 51 wherein the hydrocarbon polyradical is $C_1$ to $C_{12}$ hydrocarbon polyradical.

Embodiment 53 is a compound of embodiment 52 wherein the hydrocarbon polyradical is $C_1$ to $C_6$ hydrocarbon polyradical.

Embodiment 54 is a compound of any of the preceding embodiments wherein $R^{11}$ is $OC(O)C(R^d)=CH_2$ and wherein the $R^d$ in $R^{11}$ is H or $C_1$ to $C_4$ alkyl.

Embodiment 55 is a compound of embodiment 54 wherein $R^d$ is H or methyl.

Embodiment 56 is a compound of embodiment 55 wherein $R^d$ is H.

Embodiment 57 is a compound of embodiment 55 wherein $R^d$ is methyl.

Embodiment 58 is a compound of any of the preceding embodiments wherein $R^{12}$ is $OC(O)C(R^d)=R^a$ and wherein the $R^d$ in $R^{12}$ is H or $C_1$ to $C_4$ alkyl.

Embodiment 59 is a compound of embodiment 58 wherein $R^d$ is H or methyl.

Embodiment 60 is a compound of embodiment 59 wherein $R^d$ is H.

Embodiment 61 is a compound of embodiment 59 wherein $R^d$ is methyl.

Embodiment 62 is a compound of any of the preceding embodiments wherein $R^a$ is $N(R')_m(R^b Si(R^e)_3)_n$, and wherein R' is $C_1$ to $C_4$ alkyl.

Embodiment 62a is a compound of any of embodiments 1-61 wherein $R^a$ is $N(R')_m(R^b Si(R^{14})_3)_n$, and wherein R' is H.

Embodiment 63 is a compound of any of the preceding embodiments wherein $R^a$ is $N(R')_m(R^b Si(R^{14})_3)_n$, and wherein m is 1.

Embodiment 64 is a compound of any of embodiments 1-61 wherein $R^a$ is $N(R')_m(R^b Si(R^{14})_3)_n$, and wherein m is 0.

Embodiment 65 is a compound of any of the preceding embodiments wherein $R^a$ is $N(R')_m(R^b Si(R^{14})_3)_n$, and wherein $R^b$ is $C_1$ to $C_{12}$ alkylene.

Embodiment 66 is a compound of embodiment 65 wherein $R^b$ is $C_1$ to $C_6$ alkylene.

Embodiment 67 is a compound of any of the preceding embodiments wherein $R^a$ is $N(R')_m(R^b Si(R^{14})_3)_n$, and wherein at each occurrence of $R^{14}$ in $R^a$ is oxyalkyl or hydroxyl.

Embodiment 68 is a compound of embodiment 67 wherein the oxyalkyl is $C_1$ to $C_6$ oxyalkyl.

Embodiment 69 is a compound of embodiment 68 wherein the oxyalkyl is methyl or ethyl.

Embodiment 70 is a compound of any of the preceding embodiments wherein r is 1-6.

Embodiment 71 is a compound of any of the preceding embodiments wherein r is 1-3.

Embodiment 72 is a compound of any of the preceding embodiments wherein x is 1-3.

Embodiment 73 is a compound of any of the preceding embodiments wherein x is 1-2.

Embodiment 74 is a compound of any of the preceding embodiments wherein x is 0.

Embodiment 75 is a compound of any of the preceding embodiments wherein y is 1-3.

Embodiment 76 is a compound of any of the preceding embodiments wherein y is 1-2.

Embodiment 77 is a compound of any of the preceding embodiments wherein y is 0.

Embodiment 78 is a compound of any of embodiments 1-49 or 51-69 wherein r is 0.

Embodiment 79 is a compound of any of the preceding embodiments wherein $R_i$ is

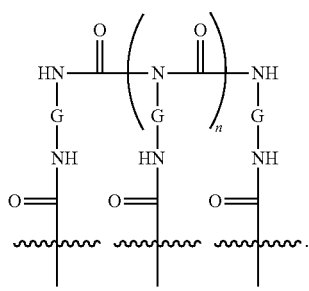

Embodiment 80 is a compound of embodiment 79 wherein n is 1-6.

Embodiment 81 is a compound of embodiment 80 wherein n is 1-3.

Embodiment 82 is a compound of embodiment 81 wherein n is 1.

Embodiment 83 is a compound of any of embodiments 1-78 wherein $R_i$ is

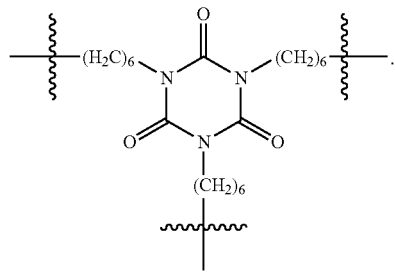

Embodiment 84 is a compound of any of embodiments 1-78 wherein $R_i$ is

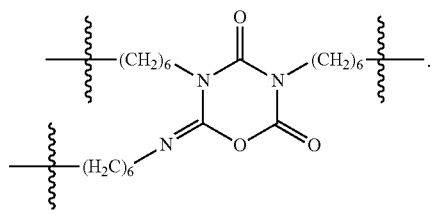

Embodiment 85 is a compound of any of embodiments 1-78 wherein $R_i$ is

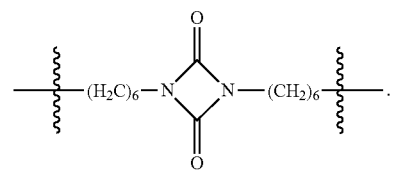

Embodiment 85a is a compound of any of embodiments 1-78 wherein $R_i$ is

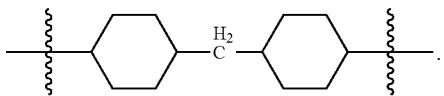

Embodiment 86 is a compound of any of the preceding embodiments wherein $R^{15}$ is $R^{13}$.

Embodiment 87 is a compound of any of the preceding embodiments wherein $R^{15}$ is alkyl.

Embodiment 88 is a compound of embodiment 87 wherein the alkyl is $C_1$ to $C_{12}$ alkyl.

Embodiment 89 is a compound of embodiment 88 wherein the alkyl is $C_1$ to $C_6$ alkyl.

Embodiment 90 is a compound of embodiment 89 wherein the alkyl is $C_1$ to $C_4$ alkyl.

Embodiment 91 is a compound of any of embodiments 1-86 wherein $R^{15}$ is H.

Embodiment 92 is a compound of any of the preceding embodiments wherein $R^{16}$ is $C_1$ to $C_{12}$ alkyl.

Embodiment 93 is a compound of embodiment 92 wherein $R^{16}$ is $C_1$ to $C_6$ alkyl.

Embodiment 94 is a compound of embodiment 93 wherein $R^{16}$ is $C_1$ to $C_4$ alkyl.

Embodiment 95 is a silica nanoparticle with a compound of any of the preceding claims affixed thereto.

Embodiment 96 is composition comprising a plurality of silica nanoparticles of embodiment 95.

Embodiment 97 is the composition of embodiment 96 further comprising one or more polymers.

Embodiment 98 is a substrate having a compound of any of claims 1-94 affixed thereto.

Embodiment 99 is a substrate of embodiment 98 wherein the substrate comprises glass or ceramic.

Embodiment 100 is a substrate of embodiment 99 wherein the substrate comprises glass.

Embodiment 101 is an article comprising a compound of any of claims 1-94, a composition of any of claims 95-97, or a substrate of any of claims 97-100.

Embodiment 102 is an article of embodiment 101 wherein the article is a molded article.

EXAMPLES

Materials 1,2,2,6,6-pentamethyl-4-hydroxy-piperidine (PMI-IP) was obtained from TCI America (Portland, Oreg., USA).

TINUVIN 123, IRGACURE 184, and IRGACURE 819 were obtained from BASF (Florham Park, USA) under trade designations "TINUVIN 123", "IRGACURE 184", and "IRGACURE 819" respectively.

1,1-bis(acryloyloxymethyl)ethyl isocyanate (BEI), isocyanatoethyl acrylate (AOI), and isocyanatoethyl methacrylate (MOI, also designated as IEM), were obtained from obtained CBC America Corp. (Commack, N.Y., USA).

TEGORAD 2100 was obtained from Evonik Corp. (Piscataway, N.J., USA) under trade designation "TEOGRAD 2100".

Tetrahydrofuran (THF), methyl ethyl ketone (MEK), methyl t-butyl ether (MTBE), sodium carbonate, sodium hydroxide, anhydrous magnesium sulfate, 85% potassium hydroxide, dimethyl sulfoxide (DMSO), methylene chloride (dichloromethane), methanol, chloroform, and triethylamine were obtained from EMD Chemicals, Inc. (Gibbstown, N.J., USA).

Hydroxyethyl acrylate (HEA), 4-methoxyphenol (MEHQ), triethylamine, dibutyltin dilaurate (DBTDL), acryloyl chloride, oxalyl chloride, and sodium cyanoborohydride were obtained from Sigma-Aldrich (Milwaukee, Wis., USA).

Ammonium acetate was obtained from VWR Scientific (West Chester, Pa., USA).

EBECRYL 600 (epoxy acrylate of the diglycidyl ether of bisphenol A), was obtained from Allnex (Alpharetta, Ga., USA) under trade designation "EBECRYL 600".

DESMODUR N100 and DESMODUR N 3600 were obtained from Bayer Polymers, LLC (Pittsburgh, Pa., USA) under trade designations "DESMODUR N100" and "DESMODUR N 3600" respectively.

Pentaerythritol triacrylate (PET3A) was obtained from Sartomer Company (Exton, Pa., USA) under the designation "SR444C".

Hexanediol diacrylate was obtained from Sartomer Company (Exton, Pa., USA) under the designation "SR238".

Acrylated benzotriazole CAS number 96478-09-0, was obtained from TCI America (Portland, Oreg., USA).

4-hydroxytempo was obtained from BASF (Florham Park, N.J., USA) under trade designation "PROSTAB 5198".

1-methoxy-2-propanol was obtained from Alfa Aesar (Ward Hill, Mass., USA).

The abbreviation "EW" is used for "equivalent weight" throughout the Examples.

Preparative Example 1

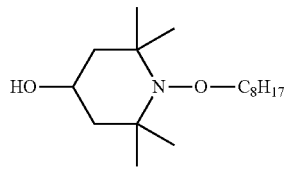

A 1 L 3-necked round bottom that is equipped with overhead stirrer and a vacuum bearing was charged with 200 g (0.275 mol, 0.55 eq, 737 MW) TINUVIN 123, and 323 g ethanol and placed in an oil bath at 70° C. To the reaction was added 73.23 g (1.109 mol, 66.01 MW) 85% potassium hydroxide. As the base was added the color of the reaction mixture changed from yellow to orange to brown; the reaction mixture also began refluxing. The bottom of the flask was scraped to provide a homogeneous mixture.

After the reaction mixture refluxed for 3.5 hours, the flask was fitted with a distillation head and condenser and placed under aspirator vacuum. 215 g of ethanol was collected by distillation, after which the reaction mixture was a thick, taffy-like mass. 250 g of water was added to the reaction mixture and the inside of the flask was scraped to disperse or dissolve the solids. The mixture was stirred for about 10 min at about 50° C., after which 300 g MTBE was added to the flask and stirred for a further 10 min. The reaction mixture was then poured into a 2 L separatory funnel, the bottom layer drained off and the top layer washed with 250 g water in the funnel. After removing the aqueous layer, the organic layer was dried over anhydrous magnesium sulfate, filtered, and concentrated on a rotary evaporator under aspirator pressure at 90° C. for 2 h to provide 137.2 g (87%) of undistilled product. This was distilled at 140° C. (pot temperature) at 29.3 Pa to provide 127.5 g (80.8%) of product.

Preparative Example 2

Preparation of a Ketone Intermediate

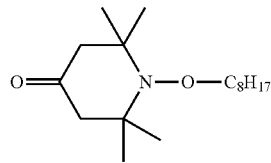

To a 500 mL 3-neck flask equipped with an over head stirrer and nitrogen inlet adapter, and a rubber septum was charged 12.04 g (0.1541 mol) dimethyl sulfoxide and 226 g of methylene chloride. The reaction was put under a nitrogen atmosphere and placed in an isopropanol-dry ice bath. After a few minutes, 9.78 g (0.0770 mol) oxalyl chloride was added via syringe through the septum over one minute. Five minutes later 20.00 g (0.0701 mol, approximate molecular weight 285.47) 2,2,6,6-tetramethyl-4-hydroxy-1-octyloxy-piperidine (the product of Preparative Example 1) was slowly added by syringe through the septum over 15 minutes. After a further 15 minutes of stirring, 17.72 g (0.17515 mol) triethylamine was added by syringe over about 30 seconds. Stirring was continued for 10 minutes in the isopropanol-dry ice bath, followed by a further 10 minutes at room temperature. The resulting solution was washed with 333 mL of 2-N hydrochloric acid, providing a mixture with distinct organic and aqueous layers. The organic and aqueous layers were separated, and the aqueous layer was extracted with 200 g of chloroform. The chloroform was combined with the other organic layer, and combined organic layers were dried over anhydrous magnesium sulfate, filtered, and concentrated on a rotary evaporator under water aspirator pressure at about 65° C. for 2 hours to provide an oil. The product was evaluated by $^1$H NMR and FTIR, which gave results consistent with the expected structure.

Preparative Example 3

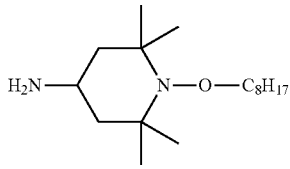

A 250 mL 3-necked flask equipped with overhead stirrer was charged with 5.00 g (0.017639 mol) 2,2,6,6-tetramethyl-4-keto-1-octyloxy-piperidine (the product of Preparative Example 2,) 8 g of 3 angstrom molecular sieves, 13.60 g (0.17639 mol) ammonium acetate, and 77.5 g methanol and stirred for 1.75 hour under nitrogen at room temperature, after which 1.51 g (0.0242 mol) sodium cyanoborohydride in 13 g methanol was added to the reaction over 45 minutes and allowed to stir overnight. 360 g chloroform was then added to the reaction mixture and the mixture was washed twice with 400 g of 1N sodium hydroxide, dried over anhydrous magnesium sulfate, filtered, and concentrated at 40° C. at aspirator pressure on a rotary evaporator. Analysis by $^1$H NMR showed the reaction to be a mixture of about 70 mole percent of the desired amine, 18 mole percent of a secondary amine, and 12 mole percent of the starting material. The products were separated by flash chromatography using an Analogix Intelliflash 280 from Agilent Technologies, Inc., Santa Clara, Calif. with a 150 g, 40 mm diameter column using a gradient of 25-30% methanol in methylene chloride over 20 minutes and then 30% methanol in methylene chloride to provide the desired product (2,2,6,6-tetramethyl-4-amino-1-octyloxy-piperidine) as an oil.

Preparative Example 4

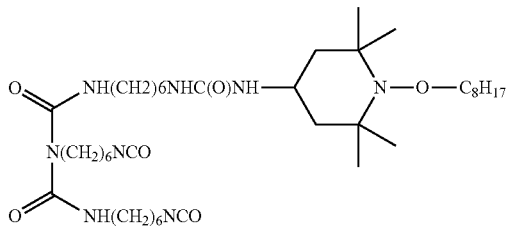

A 100 mL round bottom flask equipped with a magnetic stir bar was charged with 25.83 g (0.1345 eq, 192 EW) DESMODUR N100 and 30.00 g THF. The mixture was then swirled to dissolve the DESMODUR N100. A 25 mL pressure equalizing addition funnel was charged with 12.67 g (0.0444 eq, 285.47 EW) of the product of Preparative Example 3. The round bottom flask was placed in an ice bath and fitted with the addition funnel under dry nitrogen. The NORHALS amine was then added dropwise over 10 minutes with magnetic stirring, the addition funnel was then rinsed with 8.50 g THF. The reaction was monitored by FTIR and showed NCO absorption at 2265 cm$^1$ as static after 19 hours. After 19.5 hours, 240 microliters of a 10% by weight solution of DBTDL in THF, was charged to the reaction and the material was adjusted to 50 wt. % solids in THF.

Preparative Example 5

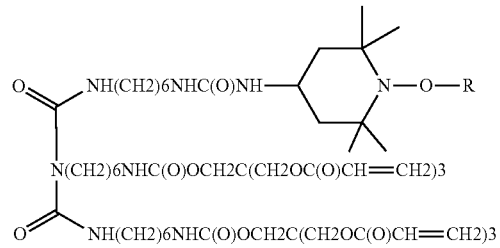

wherein R is —C$_8$H$_{17}$.

A 2 oz (59 mL) amber jar equipped with magnetic stir bar was charged with 20 g (0.0234 eq) DESMODUR N100/0.33 NORHALS amine solution of from Example 4, 11.57 g (0.0234 eq, 494.3 EW) pentaerythritol triacrylate, and 72 microliters of a 10% by weight solution of DBTDL in THF. The reaction solution was then magnetically stirred for 45 minutes in a 55° C. water bath, 11.57 g THF was charged to the jar. The reaction continued mixing and was monitored by FTIR; at 1 hour 45 minutes the material showed no NCO absorption at 2265 cm$^{-1}$. The material was then adjusted to 50% solids in THF, half was removed from the jar for later use and the remaining half was adjusted to 30% solids, 30% tetrahydrofuran and 40% isopropanol by charging 14.38 g isopropanol to the jar.

Example 1

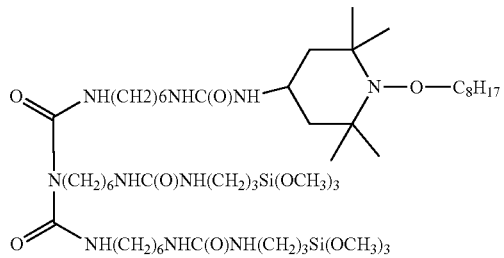

A 2 oz (59 mL) amber jar equipped with magnetic stir bar was charged with 10 g (0.0117 eq) of the product of Preparative Example 4, 13 microliters of a 10% by weight solution of DBTDL in THF, and 2.10 g (0.0117 eq, 179.3 EW) 3-aminotrimethoxysilane. The reaction solution was then magnetically stirred at room temperature for 45 minutes, after which time 2.10 g tetrahydrofuran was charged to the jar. The reaction was monitored by FTIR, at 1 hour and the material showed no isocyanate absorption at 2265 cm$^{-1}$. The material was then adjusted to 30% solids, 30% tetrahydrofuran and 40% isopropanol by charging 9.46 g isopropanol to the jar.

Example 2

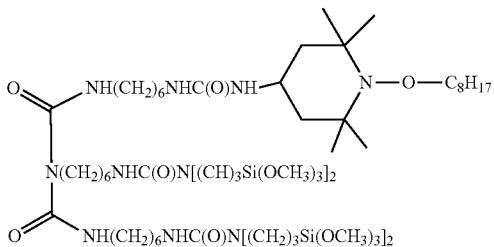

A 2 oz (59 mL) amber jar equipped with magnetic stir bar was charged with 10 g (0.0117 eq) of the product of Preparative Example 4, 25 microliters of a 10% by weight solution of DBTDL in THF, and 4.00 g (0.0117 eq, 341.5 EW) bis-(3-trimethoxysilylpropyl)amine. The reaction solution was then magnetically stirred for 45 minutes, 4.00 g tetrahydrofuran was charged to the jar. The reaction was monitored by FTIR and at 1 hour the material showed no isocyanate absorption at 2265 cm$^{-1}$. The material was then adjusted to 30% solids, 30% tetrahydrofuran and 40% isopropanol by charging 12.00 g isopropanol to the jar.

Example 3

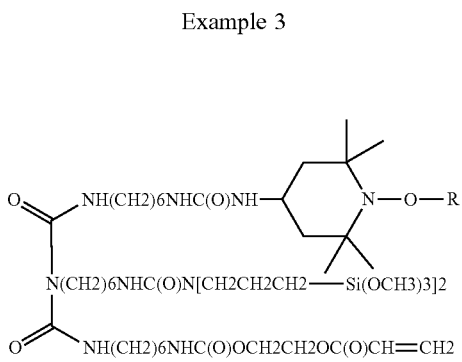

wherein R is —$C_8H_{17}$.

A 2 oz (59 mL) amber jar equipped with magnetic stir bar was charged with 10 g (0.0117 eq) of the product of Preparative Example 4, 17 microliters of a 10% by weight solution of DBTDL in THF, and 2.03 g (0.0059 eq, 341.5 EW) bis-(3-trimethoxysilylpropyl)amine. The reaction solution was then magnetically stirred for 45 minutes, 2.70 g THF was charged to the jar. The reaction was monitored by FTIR and at 1 hour and the —NCO absorption at 2265 cm$^{-1}$ was static. At 2 hours 0.67 g (0.0058 eq, 116.12 EW) hydroxyethyl acrylate was charged to the jar. The material was then mixed by stir bar at 55° C. for one hour, at which point —NCO absorption at 2265 cm$^{-1}$ was zero. The material was then adjusted to 30% solids, 30% tetrahydrofuran and 40% isopropanol by charging 10.26 g isopropanol to the jar.

Example 4

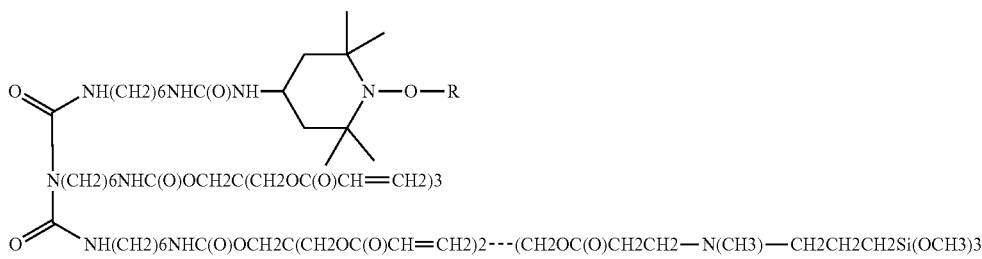

wherein R is —$C_8H_{17}$.

A 2 oz (59 mL) amber jar equipped with magnetic stir bar was charged with 21.57 g (0.0175 eq) of the product of Preparative Example 5, 1.11 g (0.0058 eq, 193.32 EW) N-methylaminopropyltrimethoxysilane, and 1.11 g THF. The reaction solution was then magnetically stirred for 1 hour at 55° C. The material was then adjusted to 30% solids, 30% THF and 40% isopropanol by charging 15.87 g isopropanol to the jar.

Example 5

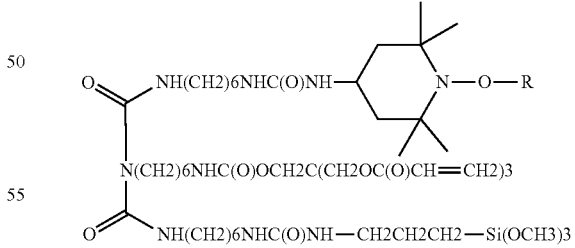

wherein R is —$C_8H_{17}$.

A 2 oz (59 mL) amber jar equipped with magnetic stir bar was charged with 10 g (0.0117 eq) of the product of Preparative Example 4, 25 microliters of a 10% by weight solution of DBTDL in THF, and 1.07 g (0.0059 eq, 179.3 EW) 3-aminotrimethoxypropylsilane. The reaction solution was then magnetically stirred for 45 minutes, 3.91 g THF was charged to the jar. The reaction was monitored by FTIR and at 1 hour the NCO absorption at 2265 cm$^{-1}$ was static.

At 2 hours 2.85 g (0.0058 eq, 494.3 EW) pentaerythritol triacrylate was charged to the jar. The material was then mixed by stir bar for 20 hours at which point the NCO absorption at 2265 cm$^{-1}$ was zero. The material was then adjusted to 30% solids, 30% tetrahydrofuran and 40% isopropanol by charging 11.89 g isopropanol to the jar.

Example 6

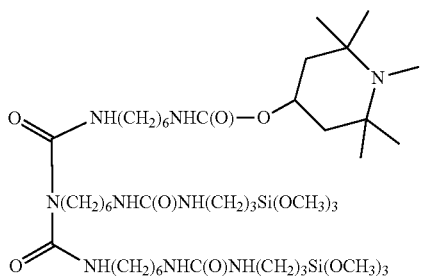

A 2 oz (59 mL) amber jar equipped with magnetic stir bar was charged with 2 g (0.0104 eq) DESMODUR N100 followed by 2 g THF. Then 1.18 g (0.0034 eq, 171.28 EW) of a 50% PHMP solution in THF was added. The solution was magnetically stirred for 4.5 hours in a 55° C. water bath. 1.25 g (0.0070 eq, 179.3 EW) 3-aminopropyltrimethoxysilane was charged to the jar, immediately followed by 1.25 g THF. The solution continued mixing overnight. The reaction was monitored by FTIR and the following morning the material showed no NCO absorption at 2265 cm$^{-1}$. The material was then adjusted to 30% solids, 30% tetrahydrofuran and 40% isopropanol by charging 5.37 g isopropanol to the jar.

Example 7

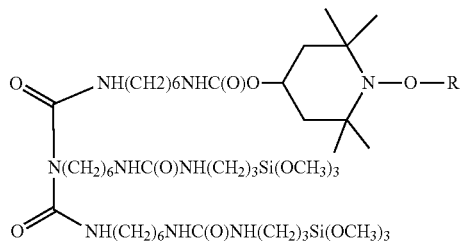

wherein R is —C$_8$H$_{17}$.

A 2 oz (59 mL) amber jar equipped with magnetic stir bar was charged with 2 g (0.0104 eq) DESMODUR N100 followed by 2 g THF, followed by 8 microliters of a 10% by weight solution of DBTDL in THF. Then 1.96 g (0.0034 eq, 286.47 EW) of a 50% NORHALS alcohol solution in THF was added. The solution was magnetically stirred for 4.5 hours in a 55° C. water bath. Then 1.25 g (0.0070 eq, 179.3 EW) 3-aminopropyltrimethoxysilane was charged to the jar, immediately followed by 1.25 g THF. The solution then continued mixing overnight. The reaction was monitored by FTIR and the following morning the material showed no NCO absorption at 2265 cm$^{-1}$. The material was then adjusted to 30% solids, 30% tetrahydrofuran and 40% isopropanol by charging 5.93 g isopropanol to the jar.

Example 8

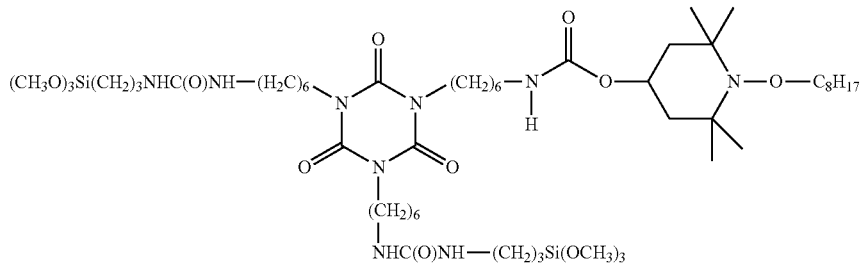

A 2 oz (59 mL) amber jar equipped with magnetic stir bar was charged with 6 g (0.0166 eq) of a 50% solution of DESMODUR N3600 in THF. Then 3.13 g (0.0034 eq, 171.28 EW) of a 50% solution of the product of Preparative Example 1 in THF was added, followed by 40 microliters of a 10% by weight solution of DBTDL in THF. The solution was magnetically stirred overnight in a 55° C. water bath. 1.99 g (0.0111 eq, 179.3 EW) 3-aminopropyltrimethoxysilane was charged to the jar, immediately followed by 1.99 g THF. The solution was mixed for five minutes producing a white solid. The reaction was monitored by FTIR and at this point the material showed no NCO absorption at 2265 cm$^{-1}$. The material was then adjusted to 30% solids, 30% tetrahydrofuran and 40% isopropanol by charging 9.18 g isopropanol to the jar.

Example 9

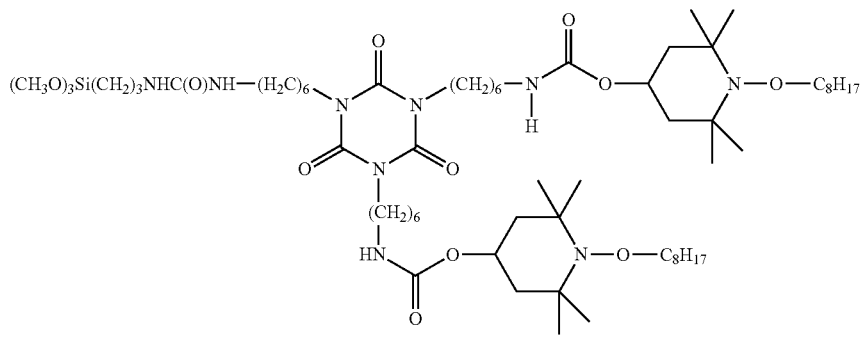

A 2 oz (59 mL) amber jar equipped with magnetic stir bar was charged with 6 g (0.0166 eq) of a 50% solution of DESMODUR N3600 in THF. Then 6.36 g (0.0111 eq, 171.28 EW) of a 50% solution of the product of Preparatory Example 1 in THF was added, followed by 45 microliters of a 10% by weight solution of DBTDL in THF. The solution was magnetically stirred overnight in a 55° C. water bath. 0.98 g (0.0055 eq, 179.3 EW) was charged to the jar, immediately followed by 0.98 g THF. The reaction was monitored by FTIR and after mixing five minutes the material showed no NCO absorption at 2265 cm$^{-1}$. The material was then adjusted to 30% solids, 30% tetrahydrofuran and 40% isopropanol by charging 10.02 g isopropanol to the jar.

What is claimed is:
1. A compound having the structure of Formula (I):

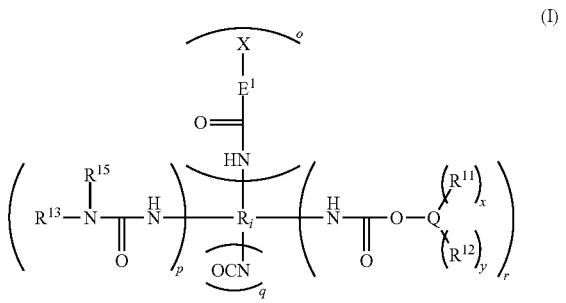

(I)

wherein
$R_i$ is a residue of a multi-isocyanate;
$E^1$ is O or NR',
R' is H or $C_1$ to $C_4$ alkyl;
X is

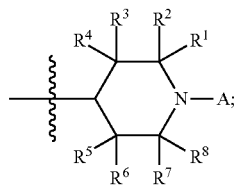

$R^1$ is alkyl;
$R^2$ is alkyl;
$R^3$ is H or alkyl;
$R^4$ is H or alkyl;
$R^5$ is H or alkyl;
$R^6$ is H or alkyl;
$R^7$ is alkyl;
$R^8$ is alkyl;
A is alkyl or oxyalkyl;
o is the number of NHC(O)E$^1$X groups bound to $R_i$, which is between 1 and 9;
each Q is independently a connecting group having a valence of x+y+1;
each $R^{11}$ is independently an (alkyl)acrylolyoxy functional group of the formula OC(O)C(R$^d$)=CH$_2$, wherein each R$^d$ is independently alkyl or H;
x is the number of $R^{11}$ groups attached to a Q, which is from 0 to 6;
y is the number of $R^{12}$ groups attached to a Q, which is from 0 to 6;
each $R^{12}$ is independently —OC(O)CH(R$^d$)CH$_2$—R$^a$ wherein R$^d$ is defined as above;
R$^a$ is N(R$^{16}$)$_m$(R$^b$Si(R$^{14}$)$_3$)$_n$;
$R^{16}$ is alkyl;
R$^b$ is alkylene that is also bound to the Si atom of Si(R$^{14}$)$_3$;
each $R^{14}$ is independently selected from alkyl, oxyalkyl, OC(O)R$^d$, and hydroxyl, with the proviso that at least one $R^{14}$ is oxyalkyl, OC(O)R$^d$, or hydroxyl;
m is the number of $R^{16}$ groups bound to N, which is 0-1;
n is the number of R$^b$ groups bound to N, which is 1 or 2;
r is the number of

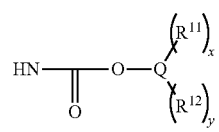

groups attached to $R_i$, which is from 0 to 6;
each $R^{13}$ is independently R$^c$Si(R$^{14}$)$_3$;
each R$^c$ is independently alkylene, alkylene amine alkylene, or alkylene amine alkylene amine alkylene that is also bound to the Si atom of Si(R$^{14}$)$_3$;
each $R^{15}$ is independently $R^{13}$, H, or alkyl;
p is the number of $R^{13}(R^{15})$NC(O)NH groups bound to $R_i$, which is from 0 to 9;
q is the number of NCO groups covalently bound to $R_i$, which is from 0 to 8;

with the proviso that the sum of p+q+o+r is from 2 to 10;
with the proviso that the sum of p and y is at least 1; and
if x or y is at least 1, then r is at least 1.

2. A compound of claim 1 wherein $E^1$ is O.
3. A compound of claim 1 wherein $E^1$ is NR'.
4. A compound of claim 1 wherein A is $C_1$ to $C_6$ alkyl.
5. A compound of claim 1 wherein A is $C_1$ to $C_{12}$ oxyalkyl.
6. A compound of claim 1 wherein Q is hydrocarbon polyradical.
7. A compound of claim 1 wherein p is 1 or greater.
8. A compound of claim 1 wherein r is 1 or greater.
9. A compound of claim 1 wherein r is 1 or greater and p is 1 or greater.
10. A compound claim 1 wherein r is 0.
11. A compound of claim 1 wherein p is 0.
12. A silica nanoparticle having one or more compounds of claim 1 affixed thereto.
13. A composition comprising one or more silica nanoparticles of claim 12 and at least one polymer.
14. A substrate having a compound of claim 1 affixed thereto.

\* \* \* \* \*

UNITED STATES PATENT AND TRADEMARK OFFICE
CERTIFICATE OF CORRECTION

PATENT NO. : 10,000,626 B2
APPLICATION NO. : 15/532663
DATED : June 19, 2018
INVENTOR(S) : Thomas Klun Page 1 of 2

It is certified that error appears in the above-identified patent and that said Letters Patent is hereby corrected as shown below:

On the Title Page

Column 1 (Notice)
Line 3, after "0 days." delete "days.".

In the Specification

Column 2
Line 30, delete "(alkyl)acrylolyoxy" and insert -- (alkyl)acryloyloxy --, therefor.

Column 9
Line 30, delete "bis(alkyated" and insert -- bis(alkylated --, therefor.

Line 37-45 (approx.), delete " 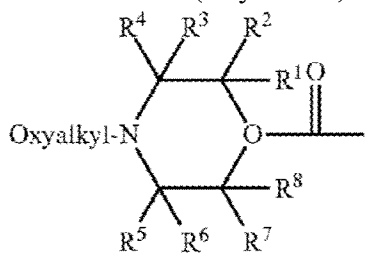 " and insert -- 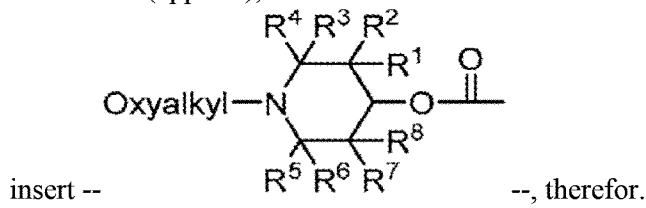 --, therefor.

Column 10
Line 53, delete "N-Akyl" and insert -- N-Alkyl --, therefor.

Signed and Sealed this
Twenty-eighth Day of August, 2018

Andrei Iancu
*Director of the United States Patent and Trademark Office*

CERTIFICATE OF CORRECTION (continued)
U.S. Pat. No. 10,000,626 B2

Page 2 of 2

Column 11
Line 6 (approx.), delete "N-Oxyakyl" and insert -- N-Oxyalkyl --, therefor.
Line 17 (approx.), delete "N-Oxylkyl" and insert -- N-Oxyalkyl --, therefor.
Line 46, delete "cyannoborohydride" and insert -- cyanoborohydride --, therefor.

Column 12
Line 35, delete "Oxyalktyl" and insert -- Oxyalkyl --, therefor.
Line 47 (approx.), delete "N-Oxylkyl" and insert -- N-Oxyalkyl --, therefor.

Column 17
Line 5, delete "di-2-ethylexanoate," and insert -- di-2-ethylhexanoate, --, therefor.

Column 18
Line 21 (approx.), delete "(meth)acrylolyoxy" and insert -- (meth)acryloyloxy --, therefor.
Line 26, delete "alkyleneneaminoalkylene," and insert -- alkyleneaminoalkylene, --, therefor.

Column 25
Line 21 (approx.), delete "$R^cSi(R^{14})_3$." and insert -- $R^cSi(R^{14})_3$. --, therefor.

Column 27
Line 51, delete "(alkyl)acrylolyoxy" and insert -- (alkyl)acryloyloxy --, therefor.

Column 32
Line 54, delete "(PMI-IP)" and insert -- (PMHP) --, therefor.

In the Claims

Column 42
Line 31, In Claim 1, delete "(alkyl)acrylolyoxy" and insert -- (alkyl)acryloyloxy --, therefor.

Column 43
Line 14, In Claim 10, after "compound" insert -- of --.